United States Patent
Shusta et al.

(10) Patent No.: US 8,034,607 B2
(45) Date of Patent: Oct. 11, 2011

(54) METHODS OF ENHANCED HETEROLOGOUS PROTEIN SECRETION

(75) Inventors: Eric V. Shusta, Madison, WI (US); Alane E. Wentz, Graftin, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 221 days.

(21) Appl. No.: 12/209,656

(22) Filed: Sep. 12, 2008

(65) Prior Publication Data

US 2009/0258388 A1 Oct. 15, 2009

Related U.S. Application Data

(60) Provisional application No. 60/971,748, filed on Sep. 12, 2007.

(51) Int. Cl.
  *C12N 9/60* (2006.01)
  *C12N 15/12* (2006.01)
  *C12N 1/16* (2006.01)
  *A61K 38/00* (2006.01)

(52) U.S. Cl. ............ 435/254.2; 435/69.6; 435/224; 435/483; 536/360; 536/300; 536/388.2

(58) Field of Classification Search .............. None
See application file for complete search history.

(56) References Cited

U.S. PATENT DOCUMENTS

| | | | |
|---|---|---|---|
| 5,773,245 A | 6/1998 | Wittrup et al. | |
| 6,300,065 B1 | 10/2001 | Kieke et al. | |
| 6,361,964 B1 * | 3/2002 | Kaiser et al. | 435/68.1 |
| 6,423,538 B1 | 7/2002 | Wittrup et al. | |
| 6,476,194 B1 * | 11/2002 | Tessier et al. | 530/350 |
| 6,696,251 B1 | 2/2004 | Wittrup et al. | |
| 6,699,658 B1 | 3/2004 | Wittrup et al. | |
| 6,759,243 B2 | 7/2004 | Kranz et al. | |

OTHER PUBLICATIONS

Pie et al. (2003) Using protein design for homology detection and active site searches, Proc. Natl. Acad. Sic. USA, vol. 100, No. 20, pp. 11361-11366.*
Laurio K. (1997) functional remote protein homology with hidden Markov models, Dissertation, University of Skovde, Sweden, pp. 1-81.*
Lodi et al. (2005) Secretion of human serum albumin by Kluyveromyces lactis overexpressing KIPDI1 and KIERO1, Appl. Environ. Microbiol., vol. 71, No. 8, pp. 4359-4363.*
Genetic Testing (2010, updated) www.thegenetictesting.com/, pp. 1-4.*
Wu et al. (2008) Differential control of Zap1-regulated genes in response to zinc deficiency in Saccharomyces cerevisiae, BMC Genomics, vol. 9, No. 370, pp. 1-17.*
Mateo M. (May 17, 2007) "Important of CCW12 gene expression in zinc deficient Saccharomyces cerevisiae", pp. 1-15 [page number not labeled]).*
Shusta E.V. (2005) Oral presentation "RAFT VII", http://sim.confex.com/sim/raft7/preliminaryprogram/abstract_4466.htm, Title "Yeast Cellular Engineering for Increased Heterologous Protein Production", p. 1.*
Attachment Shuata EV-III (2005) Yeast Cellular Engineering for Increased Heterologous Protein Production, p. 1.*
Attachment Shuata EV-I (2005) RAFT VII, p. 1.*
Attachment Shuata EV-II (2005) Fermentation Process and Product Improvement—Advancements in physiology and metabolic studies, p. 1.*
1. Shusta, E. V. et al. 1998, Nat Biotechnol 16:773-7.
2. Shusta, E. V. et al. 2000. Nat Biotechnol 18:754-9.
3. Shusta, E. V. et al. 1999. J Mol Biol 292:949-56.
4. Huang, D. and Shusta, E. V. Biotechnol Prog. 2005. 21(2)349-57.
5. Huang, D. And Shusta, E. V. Appl Environ Microbiol. 2006. 72(12)7748-59.
Pavoor, T. and Shusta, E. V. Protein Engineering Strategies for the Creation of Fluorescent Biosensors, Talk at 2007 Annual AICHE Meeting, Nov. 4, 2007.
Pavoor, T. and Shusta, E. V. Protein Engineering & Applications, Talk at 2007 Annual AICHE Meeting, Nov. 5, 2007.
Pavoor, T. and Shusta, E. V. Creation of a Fluorescent Protein Biosensor, Talk at 2007 Annual AICHE Meeting, Nov, 5, 2007.
Wentz, A.E., et al., "A novel high-throughout screen reveals yeast genes that increase secretion of heterologous proteins," Appl. Environ. Microbiol. Feb. 2007; 73(4)1189-09. Epub Dec. 22, 2006.
Wentz, A.E., et al.. "Enhanced secretion of heterologous proteins from yeast by overexpression of ribosomal subunit RPP0, " Biotechnol. Prog. May-Jun. 2008; 24(3):748-56.

* cited by examiner

*Primary Examiner* — Anand Desai
*Assistant Examiner* — Samuel Liu
(74) *Attorney, Agent, or Firm* — Quarles & Brady, LLP

(57) ABSTRACT

A method of enhancing heterologous protein secretion in a yeast cell is disclosed. In one embodiment, the method comprising the steps of engineering a yeast cell to overexpress at last one gene selected from the group consisting of CCW12, CWP2, SED1, RPP0, ERO1 and their homologs, supplying the yeast cell with a nucleic acid encoding a heterologous protein and obtaining increased expression of the heterologous protein, wherein the expression is increased relative to the protein expression in a yeast cell that does not overexpress a gene selected from the group consisting of CCW12, CWP2, SED1, RPP0, ERO1 and their homologs.

17 Claims, 13 Drawing Sheets

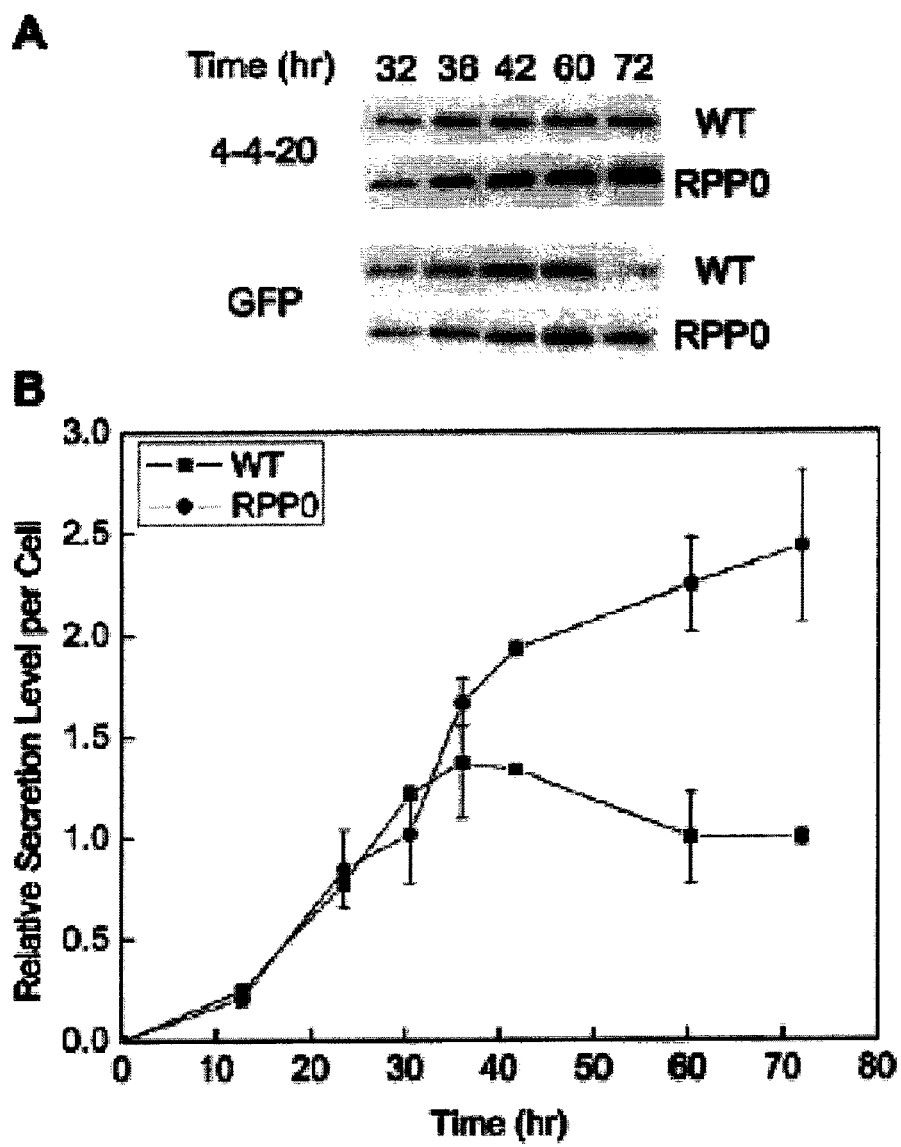
FIG. 7A-B

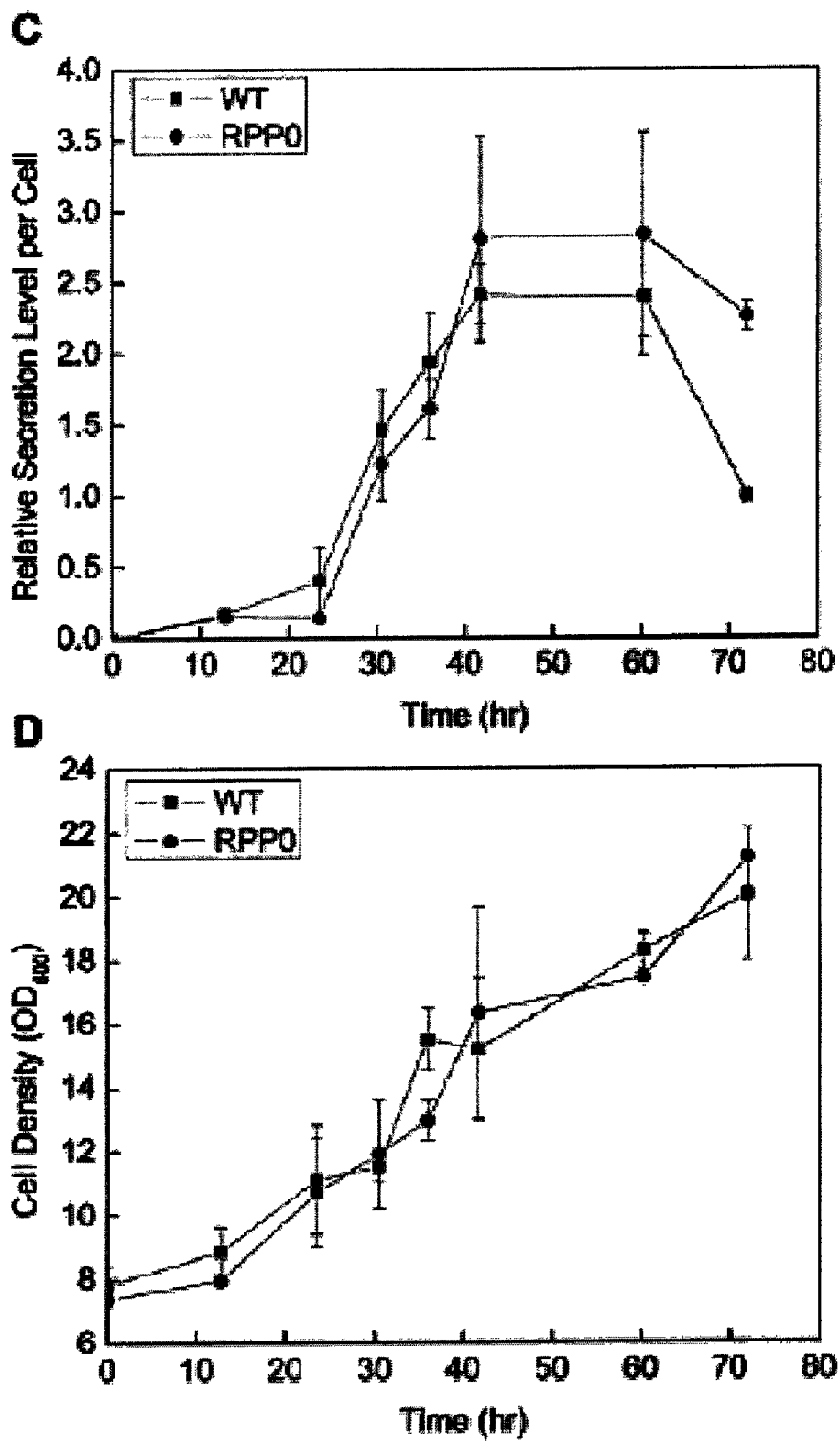
FIG. 7C-D

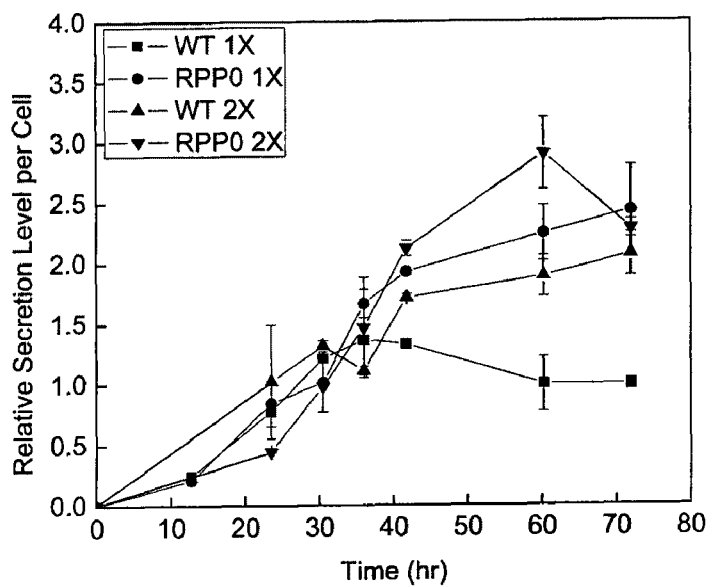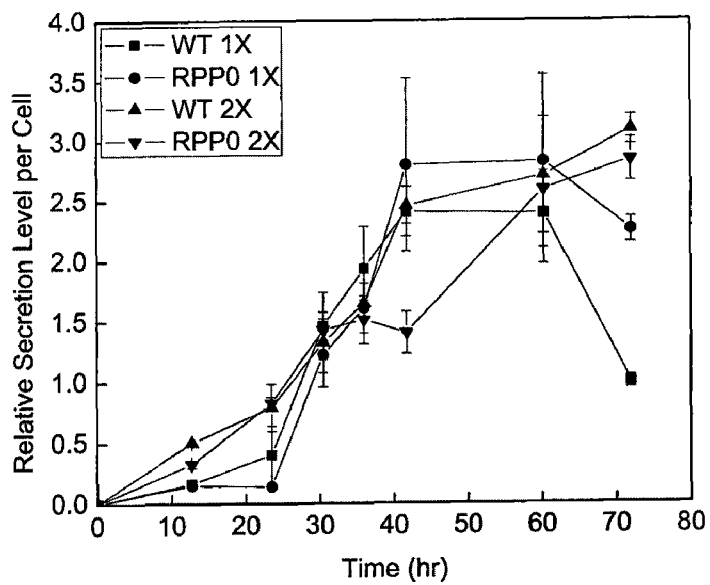
FIG. 10

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Sequencing Primer
<220> FEATURE:
<221> NAME/KEY: primer_bind
<222> LOCATION: (1)..(20)

<400> SEQUENCE: 1
tacttcttat tcctctaccg                                          20

<210> SEQ ID NO 2
<211> LENGTH: 20
<212> TYPE: DNA
<213> ORGANISM: Artificial Sequence
<220> FEATURE:
<223> OTHER INFORMATION: ACT1 Expression Primer
<220> FEATURE:
<221> NAME/KEY: primer_bind
<222> LOCATION: (1)..(20)

<400> SEQUENCE: 2
tttgtccttg tactcttccg                                          20

<210> SEQ ID NO 3
<211> LENGTH: 20
<212> TYPE: DNA
<213> ORGANISM: Artificial Sequence
<220> FEATURE:
<223> OTHER INFORMATION: ACT1 Expression Primer
<220> FEATURE:
<221> NAME/KEY: primer_bind
<222> LOCATION: (1)..(20)

<400> SEQUENCE: 3
gtaaattgga acgacgtgag                                          20

<210> SEQ ID NO 4
```

```
<211> LENGTH: 21
<212> TYPE: DNA
<213> ORGANISM: Artificial Sequence
<220> FEATURE:
<223> OTHER INFORMATION: NHA 1 Expression Primer
<220> FEATURE:
<221> NAME/KEY: primer_bind
<222> LOCATION: (1)..(21)

<400> SEQUENCE: 4
gttacgatgg agaagagaca g                                              21

<210> SEQ ID NO 5
<211> LENGTH: 20
<212> TYPE: DNA
<213> ORGANISM: Artificial Sequence
<220> FEATURE:
<223> OTHER INFORMATION: NHA1 Expression Primer
<220> FEATURE:
<221> NAME/KEY: primer_bind
<222> LOCATION: (1)..(20)

<400> SEQUENCE: 5
ccaggtttca tttcttcctc                                                20

<210> SEQ ID NO 6
<211> LENGTH: 20
<212> TYPE: DNA
<213> ORGANISM: Artificial Sequence
<220> FEATURE:
<223> OTHER INFORMATION: PMA1 Expression Primer
<220> FEATURE:
<221> NAME/KEY: primer_bind
<222> LOCATION: (1)..(20)

<400> SEQUENCE: 6
tattgttact gtcgtccgtg                                                20

<210> SEQ ID NO 7
<211> LENGTH: 20
<212> TYPE: DNA
<213> ORGANISM: Artificial Sequence
<220> FEATURE:
<223> OTHER INFORMATION: PMA1 Expression Primer
<220> FEATURE:
<221> NAME/KEY: primer_bind
<222> LOCATION: (1)..(20)

<400> SEQUENCE: 7
gcttaccgtt catcaatctg                                                20

<210> SEQ ID NO 8
<211> LENGTH: 20
<212> TYPE: DNA
<213> ORGANISM: Artificial Sequence
<220> FEATURE:
<223> OTHER INFORMATION: RPPO Expression Primer
<220> FEATURE:
<221> NAME/KEY: primer_bind
<222> LOCATION: (1)..(20)

<400> SEQUENCE: 8
gtgttcccat cttctatctt                                                20

<210> SEQ ID NO 9
<211> LENGTH: 20
<212> TYPE: DNA
<213> ORGANISM: Artificial Sequence
<220> FEATURE:
<223> OTHER INFORMATION: RPPO Expression Primer
```

```
<220> FEATURE:
<221> NAME/KEY: primer_bind
<222> LOCATION: (1)..(20)

<400> SEQUENCE: 9
gtgaccgaca gatggcaagg                                                 20

<210> SEQ ID NO 10
<211> LENGTH: 402
<212> TYPE: DNA
<213> ORGANISM: Saccharomyces cerevisiae
<220> FEATURE:
<221> NAME/KEY: gene
<222> LOCATION: (1)..(402)
<223> OTHER INFORMATION: CCW12  (Cell Wall Protein) Gene

<400> SEQUENCE: 10 atgcaattt  ctactgtcgc ttctatcgcc gctgtcgccg ctgtcgcttc tgccgctgct     60
aacgttacca ctgctactgt cagccaagaa tctaccactt ggtcaccat cacttcttgt    120 gaagaccacg tctgttctga aactgtctcc ccagctttgg tttccaccgc taccgtcacc   180
gtcgatgacg ttatcactca atacaccacc tggtgcccat tgaccactga agccccaaag   240
aacggtactt ctactgctgc tccagttacc tctactgaag ctccaaagaa caccacctct   300
gctgctccaa ctcactctgt cacctcttac actggtgctg ctgctaaggc tttgccagct   360
gctggtgctt tgttggctgg tgccgctgct ttgttgttgt aa                       402

<210> SEQ ID NO 11
<211> LENGTH: 939
<212> TYPE: DNA
<213> ORGANISM: Saccharomyces cerevisiae
<220> FEATURE:
<221> NAME/KEY: gene
<222> LOCATION: (1)..(939)
<223> OTHER INFORMATION: RPP0 (ribosomal protein P0) Gene

<400> SEQUENCE: 11
atgggaggca ttcgtgaaaa gaaagctgaa tactttgcta aattaagaga atacttggaa     60
gaatacaagt cttttgttcgt tgttggtgtt gacaatgttc cttcccaaca aatgcacgaa   120
gtcagaaagg aattgagagg cagagctgtc gtcttgatgg gtaagaacac catggttaga   180
agagccatca gaggtttctt atccgacttg ccagacttcg aaaagttgtt gccttttgtc   240
aaaggtaacg ttggtttcgt tttcactaac gaaccattga ctgaaatcaa gaacgttatt   300
gtctctaaca gagttgctgc tccagccaga gctggtgccg ttgctccaga agacatctgg   360
gttagagccg tcaacactgg tatggaacca ggtaagactt cttttcttcca agctttgggt   420 gtcccaacca agattgccag aggtaccatt gaaattgttt ctgatgtcaa ggtcgttgac   480
gccggtaaca aggtcggtca atctgaagct tccttgttga acttgttgaa catctctcca   540
ttcactttcg gtttgactgt tgttcaagtt tacgacaacg tcaagtgtt cccatcttct   600 atcttggata tcaccgatga agaattggtt tctcacttcg tttccgctgt cagcaccatt   660
gcttctatct ctttggctat tggttaccca accttgccat ctgtcggtca cactttgatc   720
aacaactaca aggacttgtt agctgttgcc attgctgctt cctaccacta ccctgaaatt   780
gaagatttgg ttgacagaat tgaaaaccca gaaaagtacg ctgctgctgc tccagctgct   840
acctccgctg cttccggtga cgctgctcca gctgaagaag ctgctgctga agaagaagaa   900
gaatctgatg acgacatggg tttcggttta ttcgattaa                          939

<210> SEQ ID NO 12
```

```
<211> LENGTH: 1692
<212> TYPE: DNA
<213> ORGANISM: Saccharomyces cerevisiae
<220> FEATURE:
<221> NAME/KEY: gene
<222> LOCATION: (1)..(1692)
<223> OTHER INFORMATION: ERO1 (Endoplasmic Reticulum Oxidoreductin 1)
      Gene

<400> SEQUENCE: 12
atgagattaa gaaccgccat tgccacactg tgcctcacgg cttttacatc tgcaacttca      60
aacaatagct acatcgccac cgaccaaaca caaaatgcct taatgacac tcacttttgt     120 aaggtcgaca ggaatgatca cgttagtccc agttgtaacg taacattcaa tgaattaaat     180
gccataaatg aaaacattag agatgatctt tcggcgttat taaaatctga tttcttcaaa     240
tactttcggc tggatttata caagcaatgt tcattttggg acgccaacga tggtctgtgc     300
ttaaaccgcg cttgctctgt tgatgtcgta gaggactggg atacactgcc tgagtactgg     360
cagcctgaga tcttgggtag tttcaataat gatacaatga aggaagcgga tgatagcgat     420
gacgaatgta agttcttaga tcaactatgt caaaccagta aaaaacctgt agatatcgaa     480
gacaccatca actactgtga tgtaaatgac tttaacggta aaaacgccgt tctgattgat     540
ttaacagcaa atccggaacg atttacaggt tatggtggta agcaagctgg tcaaatttgg     600
tctactatct accaagacaa ctgttttaca attggcgaaa ctggtgaatc attggccaaa     660
gatgcatttt atagacttgt atccggtttc catgcctcta tcggtactca cttatcaaag     720
gaatatttga acacgaaaac tggtaaatgg gagcccaatc tggatttgtt tatggcaaga     780
atcgggaact ttcctgatag agtgacaaac atgtatttca attatgctgt tgtagctaag     840
gctctctgga aaattcaacc atatttacca gaattttcat tctgtgatct agtcaataaa     900
gaaatcaaaa acaaaatgga taacgttatt tcccagctgg acacaaaaat ttttaacgaa     960
gacttagttt ttgccaacga cctaagtttg actttgaagg acgaattcag atctcgcttc    1020
aagaatgtca cgaagattat ggattgtgtg caatgtgata gatgtagatt gtggggcaaa    1080
attcaaacta ccggttacgc aactgccttg aaaattttgt ttgaaatcaa cgacgctgat    1140
gaattcacca aacaacatat tgttggtaag ttaaccaaat atgagttgat tgcactatta    1200 cagacttttcg gtagattatc tgaatctatt gaatctgtta acatgttcga aaaaatgtac    1260
gggaaaaggt taaacggttc tgaaaacagg ttaagctcat tcttccaaaa taacttcttc    1320
aacattttga aggaggcagg caaatcgatt cgttacacca tagagaacat caattccact    1380
aaagaaggaa agaaaaagac taacaattct caatcacatg tatttgatga tttaaaaatg    1440
cccaaagcag aaatagttcc aaggccctct aacggtacag taaataaatg gaagaaagct    1500
tggaatactg aagttaacaa cgttttagaa gcattcagat ttatttatag aagctatttg    1560
gatttaccca ggaacatctg ggaattatct ttgatgaagg tatacaaatt ttggaataaa    1620
ttcatcggtg ttgctgatta cgttagtgag gagacacgag agcctatttc ctataagcta    1680
gatatacaat aa                                                        1692

<210> SEQ ID NO 13
<211> LENGTH: 279
<212> TYPE: DNA
<213> ORGANISM: Saccharomyces cerevisiae
<220> FEATURE:
<221> NAME/KEY: gene
<222> LOCATION: (1)..(279)
<223> OTHER INFORMATION: CWP2 (Cell Wall Protein) Gene

<400> SEQUENCE: 13
```

```
atgcaattct ctactgtcgc ttccgttgct ttcgtcgctt tggctaactt tgttgccgct    60
gaatccgctg ccgccatttc tcaaatcact gacggtcaaa tccaagctac taccactgct   120
accaccgaag ctaccaccac tgctgcccca tcttccaccg ttgaaactgt ttctccatcc   180
agcaccgaaa ctatctctca acaaactgaa aatggtgctg ctaaggccgc tgtcggtatg   240
ggtgccggtg ctctagctgc tgctgctatg ttgttataa                          279

<210> SEQ ID NO 14
<211> LENGTH: 1017
<212> TYPE: DNA
<213> ORGANISM: Saccharomyces cerevisiae
<220> FEATURE:
<221> NAME/KEY: gene
<222> LOCATION: (1)..(1017)
<223> OTHER INFORMATION: SED1 (Cell Wall Protein) Gene

<400> SEQUENCE: 14
atgaaattat caactgtcct attatctgcc ggtttagcct cgactacttt ggcccaattt    60
tccaacagta catctgcttc ttccaccgat gtcacttcct cctcttccat ctccacttcc   120
tctggctcag taactatcac atcttctgaa gctccagaat ccgacaacgg taccagcaca   180
gctgcaccaa ctgaaacctc aacagaggct ccaaccactg ctatcccaac taacggtacc   240
tctactgaag ctccaaccac tgctatccca actaacggta cctctactga agctccaact   300
gatactacta ctgaagctcc aaccaccgct cttccaacta acggtacttc tactgaagct   360
ccaactgata ctactactga agctccaacc accggtcttc caaccaacgg taccacttca   420
gctttcccac caactacatc tttgccacca agcaacacta ccaccactcc tccttacaac   480
ccatctactg actacaccac tgactacact gtagtcactg aatatactac ttactgtcca   540
gaaccaacca ctttcaccac aaacggtaag acttacaccg tcactgaacc aaccacattg   600
actatcactg actgtccatg caccattgaa aagccaacaa ccacatcaac caccgaatac   660
actgtagtca ctgagtacac tacttactgt ccagaaccaa ccactttcac cacaaacggt   720
aagacttaca ccgtcactga accaaccact ttgactatca ctgactgtcc atgtactatt   780
gaaaagagcg aagcccctga gtcttctgtc ccagttaccg aatctaaggg cactaccacc   840
aaagaaacag gtgttactac caaacaaacc acagccaacc caagtctaac cgtctccaca   900
gtcgtcccag tttcatcctc tgcttcttct cattccgttg tcatcaacag taacggtgct   960
aacgtcgtcg ttccaggtgc tttaggtttg gctggtgttg ctatgttatt cttataa    1017
```

METHODS OF ENHANCED HETEROLOGOUS PROTEIN SECRETION

CROSS-REFERENCE TO RELATED APPLICATION

This application claims priority from U.S. provisional patent application Ser. No. 60/971,748 filed Sep. 12, 2007, incorporated by reference herein.

STATEMENT OF FEDERALLY SPONSORED RESEARCH

This invention was made, at least in part, with United States Government support awarded by National Science Foundation (NSF) award no. 0238864 (144-LQ48). The United States Government has certain rights in this invention.

BACKGROUND OF THE INVENTION

Difficulties related to heterologous protein production often limit the development of industrial and therapeutic protein products (Gerngross, T. U. 2004. Nat Biotechnol 22:1409-14). The yeast, *Saccharomyces cerevisiae*, frequently serves as a reasonable host for heterologous protein expression since this eukaryote contains much of the cellular machinery necessary to process mammalian proteins, while also being a generally regarded as safe (GRAS) organism that is easily cultured. Yet with all of these purported advantages, heterologous protein expression in yeast, in many instances, is far from optimal with yields as low as micrograms per liter (Huang, D., et al. 2006. Appl Environ Microbiol., Vol. 72, 12:099-2240; Shusta, E. V. et al. 1998. Nat Biotechnol 16:773-7). However, yeast protein production capacity in general terms is much higher given the ability to secrete certain proteins at levels approaching a gram per liter (Antoniukas, L., et al. 2006. J Biotechnol 124:347-62, 25).

The wide range of expression levels for differing protein products raises the important question as to whether cell- or protein-based factors are limiting expression. Protein engineering of a desired product has been employed to increase yeast secretion levels of various heterologous proteins including insulin precursor (Kjeldsen, T., et al. 2002. J Biol Chem 277:18245-8), barley α-amylase 2 (Fukuda, K., et al. 2005. Protein Eng Des Sel 18:515-26), and scTCR (Shusta, E. V., et al. 2000. Nat Biotechnol 18:754-9). However, this approach is highly protein-specific, introduces the possibility of deleterious functional and immunogenic alterations, and provides no guarantee of success.

As an alternative to engineering of the protein product, the host cell can be altered. Often, the host cell is subjected to multiple rounds of random mutagenesis and selection to provide for the desired increases in protein production. Although this approach can be successful, identification of the actual genetic alterations leading to increased production levels is difficult, even with the use of gene microarray analyses. As a contrasting approach, the folding and secretion apparatus of yeast can be rationally tuned by overexpression or deletion of target genes thought to play a role in protein secretion. A nonexhaustive list of examples includes the overexpression of BiP yielding increased production of scFv (Shusta, E. V., et al. 1998. Nat Biotechnol 16:773-7), and scTCR (Shusta, E. V., et al. 2000. Nat Biotechnol 18:754-9); overexpression of protein disulfide isomerase (PDI) increasing yields of scFv (Shusta, E. V., et al. 1998. Nat Biotechnol 16:773-7), granulocyte colony stimulating factor (Zhang, W., et al. 2006. Biotechnol Prog 22:1090-5), and acid phosphatase (Robinson, A. S., et al. 1994. Biotechnology (N Y) 12:381-4); and deletion of the Golgi-resident calcium ATPase, PMR1, increasing the production yields of prochymosin (Harmsen, M. M., et al. 1996. Appl Microbiol Biotechnol 46:365-70) and propapain (Ramjee, M. K., et al. 1996. Protein Eng 9:1055-61).

However, this semi-rational approach requires preliminary knowledge of potential gene targets. In addition, many of the genetic manipulations prove to be protein-specific (Butz, J. A., et al. 2003. Biotechnol Bioeng 84:292-304; Valkonen, M., et al. 2003. Appl Environ Microbiol 69:2065-72), and owing to the discrete sampling approach of this methodology, only a limited subset of yeast sequence space has been investigated. This presents a problem as a comprehensive understanding of the molecular players of the secretory pathway does not yet exist. For example the ER-associated unfolded protein response has been shown to specifically regulate the expression of 381 genes that are involved in functions ranging from transcription, folding, posttranslational modification, and vesicular trafficking, and successful mining of these pathways using a "molecule at a time" approach, although possible, is not desirable (Travers, K. J., et al. 2000. Cell 101: 249-58).

Yeast gene libraries that allow either overexpression or deletion of each of the approximately 6000 yeast gene products are available and could allow secretion analysis on a genome-wide scale that could prove beneficial for discovering multiple gene products that improve the secretory processing of proteins (Davydenko, S. G., et al. 2004. Yeast 21:463-71; Yaver, D. S., et al. 2000. Fungal Genet Biol 29:28-37). However, identifying improved yeast secretion strains requires quantitative measurement of secreted proteins by methods such as Western blotting or ELISA that tend to be prohibitive on a genome-wide scale. An alternative method that is suitable for high throughput single clone analysis is yeast surface display. Yeast surface display is accomplished by fusion of the protein of interest to an endogenous yeast protein that is shuttled through the secretory pathway and "displayed" on the yeast cell surface. Importantly, it was recently demonstrated that the surface display level of a series of mutant scTCR proteins correlated well with soluble secretion levels (Shusta, E. V., et al. 2000. Nat Biotechnol 18:754-9; Shusta, E. V., et al. 1999. J Mol Biol 292:949-56) and suggested that yeast surface display level could be used as a readout for secretion efficiency. Thus, capture of the secreted fusion protein on the surface of the cell of origin would provide a genotype-phenotoype linkage between the engineered yeast cell and protein production level. Combined with quantitative flow cytometric sorting of displaying yeast, the improved secretion strains could be evaluated on a single cell basis in rapid fashion.

We disclose herein that the yeast surface display-gene library approach was successful in identifying improved secretion strains provided an appropriate selection pressure was used. Several yeast genes that could not have been predicted a priori to impact expression were identified as suitable for enhancing the expression of heterologous proteins in a yeast cell.

BRIEF SUMMARY OF THE INVENTION

In one embodiment, the present invention is a method of enhancing heterologous protein secretion in a yeast cell comprising the steps of engineering a yeast cell to overexpress at last one gene selected from the group consisting of covalently linked cell wall protein 12 (CCW12), cell wall protein 2 (CWP2), Suppression of Exponential Defect 1 (SED1), Ribosomal Protein P0 (RPP0), Endoplasmic Reticulum Oxidoreductin 1 (ERO1) and their homologs, supplying the yeast cell with a nucleic acid encoding a heterologous protein, and obtaining increased expression of the heterologous protein, wherein the expression is increased relative to the protein expression in a yeast cell that does not overexpress a gene selected from the group consisting of CCW12, CWP2, SED1, RPP0, ERO1 and their homologs. In preferred embodiments, at least two or three genes are chosen. In another embodiment, the yeast is selected from the group consisting of S. cerevisiae, P. pastoris, and K. lactis.

In another embodiment, the gene is selected from the group consisting of CCW12, CWP2, SED1, RPPO, and ERO1 and the yeast is S. cerevisiae. In one embodiment the three genes are CCW12, ERO1, and RPPO.

In another embodiment, the heterologous protein has high basal expression levels in yeast in the absence of enhanced secretion. In another embodiment, the heterologous protein contains disulfide bonds. In a preferred embodiment the heterologous protein has a low level of expression in the absence of secretion enhancers.

In another embodiment the heterologous protein is selected from the group of those of the immunoglobulin superfamily including antibodies, T-cell receptors, MHC, cell surface receptors involved in the immune response, adhesion receptors and cytokines suck as interleukins.

In another embodiment, the present invention the protein expression is induced via an inducible promoter. In a preferred embodiment, the protein expression is increased at least 1.5, 2, or 4 fold.

In another embodiment, the present invention is a yeast cell engineered to express a heterologous protein and overexpress at least one gene selected from the group consisting of CCW12, CWP2, SED1, RPPO, ERO and their homologs.

In another embodiment, the gene is selected from the group consisting of CCW12, CWP2, SED1, RPPO, and ERO1 and the yeast is S. cerevisiae.

In another embodiment the cell is engineered to overexpress CCW12, ERO1 and RPPO.

In another embodiment, the yeast is selected from the group consisting of S. cerevisiae, P. pastoris, and K. lactis.

Other embodiments of the invention will be apparent to one of skill in the art after review of the specification, claims and drawings.

BRIEF DESCRIPTION OF THE DRAWINGS

FIG. 7A-D. Secretion time-course for 4-4-20 and green fluorescent protein (GFP). (A) Representative Western blot data was quantified to generate the secretion profiles for (B) 4-4-20 and (C) GFP. (D) Cell density for 4-4-20 secreting yeast. Growth profiles for GFP secreting yeast were identical. Protein secretion levels were measured by quantitative Western blot and normalized to cell density. Representative data in Panel A was analyzed at identical exposure times for each protein and thus can be directly compared for the given protein (4-4-20 or GFP). Shown are data corresponding to late induction times to focus on regions where secretion significantly differs. Secretion levels per cell for each analyzed protein were normalized to the WT protein levels at 72 hours. Data is representative of duplicate cultures from at least three independent experiments. WT, wild-type; RPP0, cultures overexpressing RPP0.

FIGS. 10A and B. Effects of increasing the buffering capacity of the protein induction medium. Secretion profiles for (A) 4-4-20 and (B) GFP. As with the data in FIG. 2, secretion levels were normalized to the corresponding 72 hour wild-type (WT) cultures grown in 1× medium (WT 1×). Each data point represents independent duplicate cultures.

DESCRIPTION OF THE INVENTION

Figure 1:
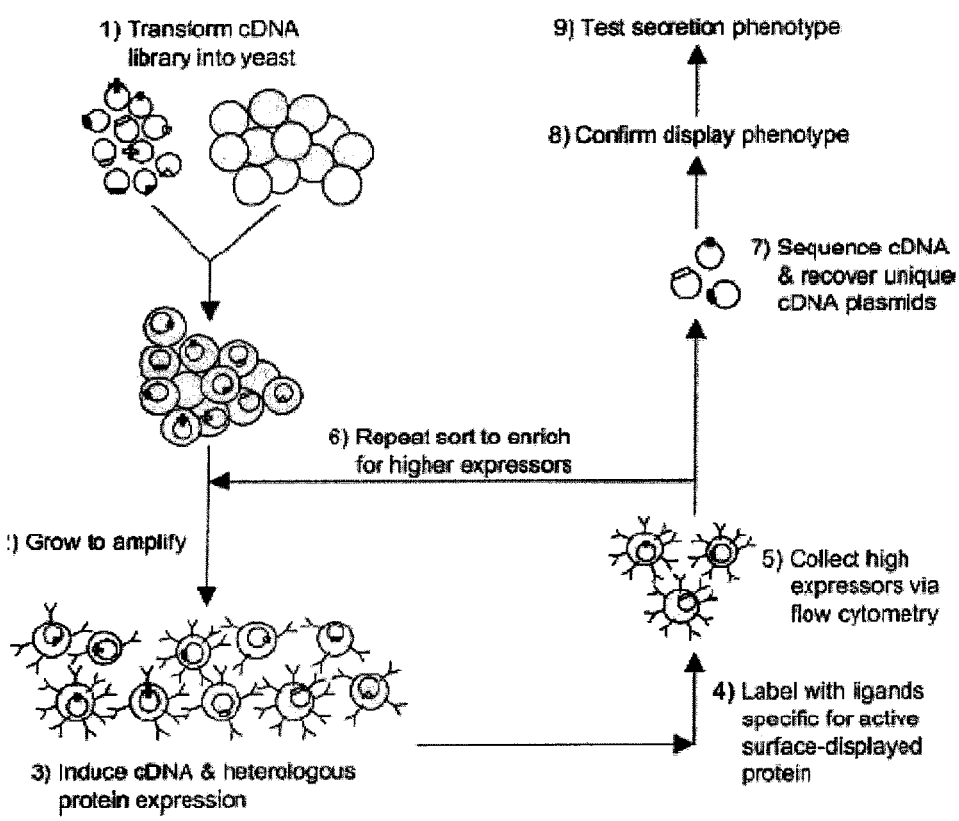
FIG. 1. Schematic of method for identification of yeast genes that elevate the yeast surface display levels of a target protein. 1) Prior to introduction of the plasmid-based cDNA library, yeast cells were transformed with a plasmid containing the protein of interest (scFv or scTCR) such that after Step 1, each cell contained two galactose-inducible plasmid constructs. 2) Cells were amplified in glucose-based media and 3) protein expression was induced in galactose-based media. Step 3 was performed under normal 20° C. induction conditions, or at elevated temperatures of 30° C. and 37° C. as described in the text. After step 3, yeast cells had varying levels of surface-displayed protein as a result of the induced genetic alteration (via the cDNA plasmid). 4) The yeast cells were then probed for active surface-tethered protein and analyzed by flow cytometry. 5) Using FACS, the cells exhibiting higher fluorescence, and thus elevated levels of surface-displayed protein, were isolated. 6) The enriched population was then cycled through the selection process again for further enrichment. 7) The display-enhancing genes were then identified and 8) the display-enhancing phenotype was confirmed. 9) Finally, the display-enhancing cDNA were tested for their effects on protein secretion.

In general, the present invention is directed to methods of enhanced heterologous protein secretion in yeast by overexpression of at least one of five identified yeast genes.

In General

The yeast *Saccharomyces cerevisiae* is an attractive host for the production of heterologous proteins. However, low yield production of many proteins (micrograms-milligrams/liter) leaves considerable room for optimization. We became interested in the problem of low yield protein production. By engineering the yeast cell via traceable genome-wide libraries, we identified 5 yeast genes that can enhance protein expression level because of their roles in the protein transcription, translation, folding and trafficking processes. Wentz and Shusta, 2007. Applied and Environmental Microb. 1189-1198, incorporated by reference herein, is an academic publication describing our endeavors and a preferred embodiment of the present invention. Examples I and II include the data presented in Wentz and Shusta, 2007 and a second, newer academic pre-publication.

One embodiment of the present invention discloses a novel approach to protein production enhancement that combines yeast cDNA overexpression libraries with yeast surface display to allow the rapid flow cytometric screening of engineered yeast for gene products that improve the display of heterologous proteins. After optimization of the screening conditions, a genome-wide scan yielded five yeast products that promoted increased display levels of a single-chain T-cell receptor (scTCR). The display-enhancing genes included cell wall proteins (CCW12, CWP2, SED1), a ribosomal subunit protein (RPP0), and an endoplasmic reticulum-resident protein (ERO1). Under the premise that yeast surface display levels could be used as a predictor of secretion efficiency, each display-enhancing gene product was tested for its ability to affect secretion levels of multiple scTCR and single-chain antibodies (scFv). All of the selected yeast gene products were shown to promote increased secretion of active protein (1.5-fold to 7.4-fold), with CCW12 and ERO1 being the most generalizable enhancers of scFv/scTCR secretion.

Therefore, the present invention discloses five yeast genes and their homologs that Applicants have shown to promote increased secretion of active protein. In one embodiment, the present invention is a method of engineering yeast cells, preferably *Saccharomyces cerevisiae*, to overexpress at least one of the five identified endogenous yeast proteins in the presence of a gene encoding a heterologous protein. The five yeast genes are described below at SEQ ID NOs:10-14.

By "heterologous protein" we mean a protein expressed from a gene sequence that has been added to the native yeast sequences. Typically, a "heterologous protein" is a non-yeast protein. However, one may wish to express a yeast protein in our system. If a yeast protein coding sequence is added to a native yeast genome, a yeast protein may be a "heterologous protein".

In another embodiment of the present invention, one would engineer the yeast cell to overexpress at least two or three of the display-enhancing gene products in concert.

The paragraphs below more specifically describe the present invention.

Suitable Yeasts.

Applicants have investigated heterologous protein expression in *Saccharomyces cerevisiae*. However, the present invention is also applicable to other yeast species, such as *Pichia pastoris, Kluyveromyces lactis*, etc. One skilled in the art would understand that many other yeast strains could be substituted as a result of the high species homology and the fact that many different yeasts have been effectively used to produce heterologous proteins.

Preferably, one would use the already identified *S. cerevisiae* version of the aforementioned secretion enhancers and introduce this version into the selected yeast species. Alternatively, one could identify and isolate the homolog of at least one of the five identified yeast genes from the yeast of interest and use the identified homolog in the expression system.

For example, if one were to use the yeast *K. lactis*, one may wish to use the genes identified in the BLAST search described below.

Preferable Protein Products

In Wentz and Shusta, 2007, applicants have provided a method of increasing production of members of the immunoglobulin fold family. Each of the five identified display-enhancing genes improved the production of these proteins. However, Applicants believe that the present invention is suitable for many different protein products.

The Examples below disclose the inventors' recent experiments with several classes of proteins. The Examples below disclose that RPPO was suitable for increasing expression of GFP. We note that GFP is a heterologous protein with very high basal secretion levels in yeast in the absence of the present invention and theorize that RPPO gene and its homolog would be especially useful in enhancing protein production from proteins that are already at a high level (eg. 3 mg/L or more from a low copy expression system in shake flask culture). ERO1 and RPPO enhanced production of BDNF (brain derived neurotrophic factor).

Use of ERO1 and homologs will likely be most effective with proteins that contain disulfide bonds, as this gene aids in the oxidative folding pathway (with yPDI). CCW12 and RPP0 seem to be somewhat generalizable secretion enhancers, with RPP0 affecting expression of all proteins tested in our lab thus far (except BPTI and LWHI scTCR).

Expression level plays a vital role in the selection process and effectiveness of said cDNA as secretion enhancers. In general, the cDNAs did little to help well-expressed proteins (GFP, LWHI, BPTI), but were very effective with the low expressed proteins (1 mg/L or less).

Preferable heterologous proteins include those of the immunoglobulin superfamily including antibodies, T-cell receptors, MHC, cell surface receptors involved in the immune response, adhesion receptors and cytokines such as interleukins Preferable Display-Enhancing Gene Homologs The present invention is suitable for the five display-enhancing genes that we isolated from *Saccharomyces* (see SEQ ID NOs:10-14, Examples Table 4) and is also suitable for homologs of these genes. By "homologs" we mean genes that are the functional equivalent of the five *Saccharomyces* yeast display-enhancing genes isolated from other species. Structurally, we believe that homologs will comprise conserved domains similar to the genes isolated from *Saccharomyces* and "positives" amino acid homology of at least 50%. However, especially in the case of the cell-wall proteins (e.g., SED1, CWP2, and CCW12), conserved domain information is unavailable, and simple amino acid homology is a useful metric for identifying homologs.

The homologs listed below have "positives" amino acid homology of at least 50%. Preferably, the homolog comprises any conserved domains known to occur in the five display-enhancing genes, such as the two pairs of conserved cysteines found in ERO1. (See Frand and Kaiser, 1998. Mol. Cell 1:161-170)

Results were generated with the BLAST program on the NCBI website (www.ncbi.nlm.nih.gov/blast/Blast.cgi?CMD=Web&PAGE TYPE=BlastHome). This program searches the protein database by translating a nucleotide query. High"Score" values correspond to higher homology, "Identity" represents the number of amino acids that are identical between the two compared sequences, and "Positives" represents the number of amino acids that are similar between the two compared sequences. The nucleotide sequence for each gene was taken from a database of yeast sequences, www.yeastgenome.org, by searching for the gene name and selecting the genomic sequence. Homologies listed below are just a few obtained from the BLAST program, and others can exist that have yet to be sequenced for a given organism, such as other yeast strains.

The cell-wall proteins are unlikely to have homologies in higher organisms (i.e., other than yeast) as other eukaryotic cells do not contain cell walls. As a result of the marginal improvements observed with cell wall proteins SED1 and CWP2 compared with the significant secretion improvement seen with CCW12, only the CCW12 gene homologies are shown below.

CCW12
Organism: *Kluyveromyces lactis*
  *K lactis*: XP_455980.1
  Protein/Gene Name: Unnamed protein product
  Score: 97.4
  Identity: 55/79 (69%)
  Positives: 62/79 (78%)
  Noted for its similarities to *S. cerevisiae* CCW12.
Organism: *Candida albicans*
  *C albicans*: EAL04558.1
  Protein/Gene Name: Potential cell wall mannoprotein
  Score: 73.2
  Identity: 37/86 (43%)
  Positives: 54/86 (62%)
  Noted for its similarities to *S. cerevisiae* CCW12.
Organism: *Pichia stipitis*
  *P stipitis*: XP_001383488.1
  Protein/Gene Name: Cell wall protein (gene CCW12)
  Score: 51.2
  Identity: 28/64 (43%)
  Positives: 41/64 (64%)
ERO1
Organism: *Kluyveromyces lactis*
  *K.lactis*: XP_453517.1

Protein/Gene Name: Endoplasmic Reticulum Oxidoreductin 1 (gene ERO1)
Score: 637
Identity: 302/531 (56%)
Positives: 400/531 (75%)
Activity of this *K. lactis* gene experimentally parallels *S. cerevisiae* ERO1 activity.
Contains the ERO1 conserved domain.
www.pubmedcentral.nih.gov/articlerender.fcqi?tool=pmcentrez&artid=1495
Alison R. Frand and Chris A. Kaiser (2000) Mol Bio Cell, v.11 (9):2833-2843
Hiniker and Bardwell (2004) Trends Bicochem Sci, 29(10):516-519
Tu and Weissmann (2004) J Cell Biol, Vol.164:341-346
Organism: *Pichia stipitis*
  *P. stipitis*: XP_001383828
  Protein/Gene Name: Endoplasmic Reticulum Oxidoreductin 1 (gene ERO1)
  Score: 306
  Identity: 198/577 (34%)
  Positives: 301/577 (52%)
  Identified as a protein required for disulfide formation in the *P. stipitis* ER.
  Contains the ERO1 conserved domain.
Organism: *Schizosaccharomyces pombe*
  *S. pombe*: NP_588313.1
  Protein/Gene Name: ERO1-like protein 2 precursor (gene ERO12)
  Score: 239
  Identity: 157/530 (29%)
  Positives: 272/530 (51%)
  Protein disulfide oxidoreductase activity inferred from genetic interactions.
  Localization to the ER determined experimentally, involvement in the secretory pathway with protein thiol-disulfide exchange and folding measured experimentally and inferred from genetic interactions. Contains the ERO1 conserved domain.
Organism: *Schizosaccharomyces pombe*
  *S. Pombe* 2: NP_596116.1
  Protein/Gene Name: ERO1-like protein 1 precursor (gene ERO11)
  Score: 215
  Identity: 123/391 (31%)
  Positives: 197/391 (50%)
  Protein disulfide oxidoreductase activity inferred from genetic interactions.
  Localization to the ER determined experimentally, involvement in the secretory pathway with protein thiol-disulfide exchange and folding measured experimentally and inferred from genetic interactions. Contains the ERO1 conserved domain.
Organism: *Mus musculus*
  Mouse NP_080460.2
  Protein/Gene Name: Endoplasmic oxidoreductase 1 beta (gene ERO1LB)
  Score: 205
  Identity: 149/419 (35%)
  Positives: 214/419 (51%)
  Named because of its homology to *S. cereviaise* ERO1, oxidoreductase activity inferred from electronic annotation. Contains the ERO1 conserved domain.
Organism: *Homo sapien*
  Human NP_063844.2
  Protein/Gene Name: Endoplasmic reticulum oxidoreductin 1-L beta (gene ERO1LB)
  Score: 202
  Identity: 144/413 (34%)
  Positives: 209/413 (50%)
  Localization to the ER determined experimentally. Function in electron transport and protein folding determined experimentally and inferred from electronic annotation. Contains the ERO1 conserved domain.
RPP0
Organism: *Kluyveromyces lactis*
  *K. lactis*: XP_451800.1
  Protein/Gene Name: Unnamed protein product
  Score: 451
  Identity: 237/273 (86%)
  Positives: 259/273 (94%)
  Noted for its similarity to *S. cerevisiae* RPP0, contains a conserved domain found in ribosomal protein L10 (original name for P0 protein) involved in translation, ribosomal structure and biogenesis.
Organism: *Pichia stipitis*
  *P. stipitis*: XP_001384996.1
  Protein/Gene Name: Ribosomal protein P0 (gene RPP0)
  Score: 405
  Identity: 235/312 (75%)
  Positives: 272/312 (87%)
  Contains conserved domains found in ribosomal protein L10 (original name for P0 protein) and 60s acidic ribosomal protein family that includes eukaryotic P0 protein.
Organism: *Candida albicans*
  *C albicans*: XP_888730.1
  Protein/Gene Name: Cytosolic ribosomal acidic protein P0
  Score: 408
  Identity: 238/312 (76%)
  Positives: 274/312 (87%)
  Noted for its similarity to *S. cerevisiae* RPP0, contains conserved domains found in ribosomal protein L10 (original name for P0 protein) and 60s acidic ribosomal protein family that includes eukaryotic P0 protein.
Organism: *Schizosaccharomyces pombe*
  *S. pombe*: NP_588393.1
  Protein/Gene Name: 60S acidic ribosomal protein P0 (gene RPP0)
  Score: 304
  Identity: 181/308 (58%)
  Positives: 233/308 (75%)
  Localization to the cytosol determined experimentally, involvement in ribosome biogenesis and assembly, translational elongation inferred from electronic annotation. Noted for its similarity to *S. cerevisiae* RPP0, contains conserved domains found in ribosomal protein L10 (original name for P0 protein) and 60s acidic ribosomal protein family that includes eukaryotic P0 protein.
Organism: *Mus musculus*
  Mouse: NP_031501.1
  Protein/Gene Name: Acidic ribosomal phosphoprotein P0 (gene ARBP, aka RPLP0)
  Score: 278
  Identity: 144/266 (54%)
  Positives: 202/266 (75%)
  Contains conserved domains found in ribosomal protein L10 (original name for P0 protein).
Organism: *Homo sapiens*
  Human: NP_000993.1
  Protein/Gene Name: Ribosomal protein P0 (gene RPLP0)
  Score: 279
  Identity: 145/266 (54%)

Positives: 202/266 (75%)

Functions in RNA binding and protein binding and structural constituent of large ribosomal subunit confirmed experimentally. Involvement in translational elongation, ribosome biogenesis and assembly, and intracellular localization inferred from electronic annotation. Contains conserved domains found in ribosomal protein L10 (original name for P0 protein).

Preferred Method of the Present Invention

Wentz and Shusta, 2007 discloses a preferred method of creating appropriate vectors for incorporation of one or more of the display-enhancing genes of the present invention and a heterologous protein sequence in a yeast species. Applicants note that other expression-vector systems would be equally suitable. By "display-enhancing genes" we mean the yeast genes SED1, CWP2, CCW12, ERO1, and RPPO. The sequences for these secretion or display-enhancing genes of their homologs can be obtained directly from the yeast genome database at www.yeastgenome.org or SEQ ID NOs: 10-14 and subcloned into low copy CEN-based vectors as in this demonstration, into 2 micron multicopy vectors, or integrated into the yeast genome.

The control of gene expression is preferably by an inducible promoter such as the GAL1-10 promoter but could also include one of the many constitutive promoters that are available. Similarly, the protein that is to be produced can be constructed in any of the aforementioned fashions.

After introduction of both the cDNAs and protein constructs into the desired yeast strain, one would induce protein expression in the case of an inducible promoter and allow protein secretion to continue over the course of 24-72 hours. Standard assays of protein concentration and activity such as Western blotting and ELISA can then be performed with the culture medium to determine protein yield. A sample detailed methodological discussion is presented in Wentz and Shusta, 2007 and Example I.

EXAMPLES

Example I

A Novel High Throughput Screen Reveals Yeast Genes that Increase Heterologous Protein Secretion Materials and Methods
Strains, Plasmids, and Media The strains and plasmids used for this study along with their sources are detailed in Table 1. Surface display data for the scFv and scTCR were obtained by transformation of pCT-OX26, pCT-7/15, pCT-LWHI or pCT-4420His6 into the following yeast strains: EBY100 (rPDI or BiP), AWY100 (yPDI), AWY101, or AWY102. EBY100 is the S. cerevisiae yeast surface display strain (Boder, E. T., et al. 1997. Nat Biotechnol 15:553-7). AWY100 was developed by changing the selectable marker for the tandem integrated AGA1 cassette from URA3 to LEU2. AWY101 and AWY102 were also generated in this study from YVH10 and BJ5464, respectively, by integrating GAL1-AGA1 in tandem with endogenous AGA1 as in the creation of EBY100. The plasmids pMAL5.1 (rPDI), pGAL-KAR2LEU (BiP), and pCT37 (yPDI) were used to increase the copy number of the corresponding folding assistants. Secreted scFv and scTCR expression data were obtained by expressing pRS-GALOX26, pRS-GALTLWHI, pRS-GALT7/15 or pRS-4420His6 in either BJ5464 or YVH10. When necessary for yeast strains harboring multiple plasmids, open reading frames were transferred to plasmid backbones possessing different auxotrophic markers. Control strains were created by transformation with null plasmids containing the identical nutritional marker (pRS-314, pRS-315, or pRS-316) (Sikorski, R. S., et al. 1989. Genetics 122:19-27). All yeast transformations were performed using the lithium acetate method (Gietz, R. D., et al. 2006. Methods Mol Biol 313:107-20) and grown in minimal medium (2% dextrose, 0.67% yeast nitrogen base) buffered at pH 6.0 with 50 mM sodium phosphate and containing either 1% casamino acids (SD-CAA, lacking tryptophan and uracil) or 2× SCAA amino acid supplement (SD-SCAA, 190 mg/L Arg, 108 mg/L Met, 52 mg/L Tyr, 290 mg/L Ile, 440 mg/L Lys, 200 mg/L Phe, 1260 mg/L Glu, 400 mg/L Asp, 480 mg/L Val, 220 mg/L Thr, 130 mg/L Gly, lacking leucine, tryptophan, and uracil). 200 mg/L leucine, 20 mg/L tryptophan, and 20 mg/L uracil were supplemented when necessary for proper auxotrophic selection. Induction of protein display and secretion was performed in the same medium with the dextrose substituted by 2% galactose. Fresh transformants were used in all experiments.

Yeast Surface Display & Library Screening

For all surface display experiments, yeast were grown for 1-2 days with shaking at 30° C. in SD-SCAA medium, and these starter cultures were subsequently diluted uniformly to 0.1 $OD_{600}$ and regrown in SD medium. When the cultures reached an $OD_{600}$ of 1-2, protein surface display was induced by changing to SG medium, and cultures were placed at the appropriate induction temperature (20°, 30°, or 37° C.) for 16-18 hours. This growth and induction method yielded optimal reproducibility in display levels between replicates and between independent experiments. Then, $2 \times 10^6$ yeast cells were collected and washed with 500 μl, PBS-BSA (PBS, pH 7.4, with 1 mg/ml bovine serum albumin, BSA) prior to immunolabeling for detection and flow cytometry. Surface displayed scFv were detected by antibody labeling with the anti-cmyc epitope tag antibody 9E10 (1:100, Covance), while scTCRs were detected with the conformationally-specific 1B2 monoclonal antibody (Manning, T. C., et al. 1998. Immunity 8:413-25) (10 μg/ml) for 30 minutes at 4° C. All samples were washed with 500 μl, PBS-BSA and subsequently labeled with anti-mouse IgG conjugated to phycoerythrin (1:35, Sigma) for 30 minutes at 4° C. After washing with 500 μl PBS-BSA, samples were resuspended in 750 μl PBS-BSA and analyzed on a Becton Dickinson FACSCalibur benchtop flow cytometer.

The cDNA overexpression library, a kind gift of Dr. Haoping Liu, consists of a pool of CEN-based plasmids, each with a single yeast open reading frame under the control of the GAL1 promoter. The plasmid library had been previously utilized in studies to analyze growth and cell cycle effects of overexpressed yeast genes (Liu, H., et al. 1992. Genetics 132:665-73; Stevenson, L. F., et al. 2001. Proc Natl Acad Sci U S A 98:3946-51). Because the library was created from yeast mRNA whose levels in the cell will vary for different genes, a minimum of 50,000 variants must be evaluated to ensure complete coverage of the yeast transcriptome (Liu, H., et al. 1992. Genetics 132:665-73). After transformation of the plasmid library into AWY100 yeast cells already transformed with the 7/15 scTCR plasmid, the yeast overexpression library contained approximately $2.3 \times 10^5$ individual clones and was screened for yeast having increased levels of 7/15 scTCR surface display (1B2 labeling). The library was oversampled by screening $8 \times 10^6$ clones using a Becton Dickinson FACSVantage SE flow cytometric sorter at the University of Wisconsin Comprehensive Cancer Center. In the first round of sorting, the top ~1% of the displaying cells were recovered and subpooled. Those subpools exhibiting the most enrichment were then carried to the next round. Subsequent rounds were performed with multiple sorting gates between 0.1-2% depending on the display distribution observed. The use of various gating percentages for rounds 2-4 helped ensure successful enrichment of the clones exhibiting improved display because relatively low absolute increases in display were being observed (1.2 to 2.5-fold). Cultures were maintained to include at least ten times the size of the library (or subsequent sorted pools) at all times. After the fourth round of enrichment, the entire sorted population was plated on nutritionally selective plates and individual clones were analyzed by flow cytometry.

Identification and Recovery of cDNA from Yeast

Clones identified as exhibiting increased 7/15 surface display via flow cytometry were spotted onto SD-SCAA plates and grown overnight. Approximately 0.2 µl cells were resuspended in 30 µl 0.2% SDS. Cells were lysed by incubating samples at −80° C. for 2 minutes, 95° C. for 2 minutes, −80° C. for 2 minutes and 95° C. for 5 minutes. Approximately 2 µl of the lysed cells were added as the DNA template to a 50 µl polymerase chain reaction (PCR) containing 0.4% Triton X-100 with Platinum Taq polymerase (Invitrogen) and the M13 primers (Liu, H., et al. 1992. Genetics 132:665-73). PCR products were run on a 1% agarose gel and bands corresponding to the cDNA inserts were visually identified.

Plasmids having uniquely-sized cDNA inserts were recovered from the yeast with the Zymoprep II Yeast Plasmid Miniprep Kit (Zymo Research). DH5α cells (Invitrogen) were used to amplify the recovered plasmid DNA and the cDNA inserts sequenced at the University of Wisconsin Biotechnology Center utilizing the 5'-TACTTCTTATTCCTC-TACCG-3' primer (SEQ ID NO:1) to obtain the forward sequence and the T7 primer (Liu, H., et al. 1992. Genetics 132:665-73) for the reverse sequence. To confirm that the increased display efficiency was the result of the harbored overexpression plasmid, the parent AWY100 strain was freshly co-transformed with each recovered cDNA-containing plasmid and pCT-7/15 and analyzed by flow cytometry as described above.

Heterologous Protein Secretion and Activity Analyses

Cultures were inoculated in SD-CAA (synthetic dextrose medium supplemented with casamino acids as an amino acid source) and allowed to grow for 1-2 days at 30° C. prior to dilution to a uniform $OD_{600}$ of 0.1 and regrowth for 3 days to an $OD_{600}$ of 8-10. Protein expression was then induced by switching to nutritionally-selective SG medium (plus 1 mg/mL BSA) and placing the cultures at 20°, 30°, or 37° C. for 3 days. Although we have previously shown 3 days to be the most general approach for maximum production (36), the growth time (1 or 3 days) and induction time (1 or 3 days) was varied for the CCW12 overexpressing, 4-4-20 system. CCW12 overexpression similarly enhanced secretion levels relative to the wild-type in all cases. In terms of absolute expression levels, the 3 day-3 day system and the 1 day-3 day system were similar, while the 1 day-1 day system was substantially lower, as expected. Therefore, throughout the manuscript, we continued to employ the 3 day-3 day system. Cell-free culture supernatants were resolved on a 12.5% polyacrylamide-SDS gel and transferred to nitrocellulose membranes. In the case of LWHI or Aga2p-scFv supernatants, samples were first deglycosylated prior to SDS-PAGE (EndoH, New England Biolabs). The membranes were probed with either anti-cmyc antibody for scFv samples (9E10, 1:3000) or anti-tetra-His antibody for LWHI scTCR samples (0.2 µg/ml, Qiagen). All membranes were probed with an anti-mouse HRP secondary antibody (1:2000, Sigma), followed by enhanced chemiluminescence detection (ECL, Amersham). Western blot films of various exposure times were analyzed with ImageJ (NIH) to determine band intensities. The slope of the intensity versus exposure time curve in the unsaturated, linear region was then utilized to determine relative protein concentrations, and hence, secretion levels. Lack of significant cell lysis was determined by probing cell supernatants for the endogenous intracellular glyceraldehyde-3-phosphate dehydrogenase (G3PDH) yeast protein. Yeast supernatants for both wild-type and CCW12-overexpressing cells were loaded onto SDS-PAGE gels along with purified G3PDH protein (Sigma) and cell lysate. After transferring to nitrocellulose, the membrane was probed with a mouse anti-yeast G3PDH antibody (1:500, Chemicon) detected via ECL as described previously, and exposed for 35 minutes. No signal was detected, and based on the sensitivity of the assay, it was determined that at the very maximum, less than 0.1% of the total heterologous protein in the supernatants could be derived from cell lysis (Huang, D., et al. 2006. Appl Environ Microbiol. Vol 72, 12:099-2240). All statistics presented in the text were determined by two-tailed unpaired student's t-test.

The 7/15 scTCR secretion levels were detected via enzyme-linked immunosorbent assay (ELISA) as the anti-tetra-His Western blot was not sensitive enough due to low 7/15 secretion levels. The ELISA also served as an activity assay since the 1B2 antibody used in detection recognizes a nearly identical epitope to that of the native peptide-major histocompatibility complex, and has proven to be a high affinity surrogate for peptide MHC (Manning, T. C., et al. 1998. Immunity 8:413-25, 34). In addition, where indicated, LWHI activity was also evaluated by ELISA to correlate increases in protein activity with increases in total protein as assessed by Western blotting. To perform the ELISA, wells of a Nunc-Immuno 96-well Maxisorp plate (Nunc) were coated with the anti-tetra-His antibody (2.7 µg/ml, Qiagen) overnight at 4° C. After blocking for 2 hours with 400 µl PBS-BT (PBS, pH 7.4, with 1 mg/ml BSA and 1 ml/L Tween 20), wells were washed four times with 250 µl PBS-BT. Various dilutions of culture supernatants were applied for 1 hour, and after four rounds of washing with PBS-BT, biotinylated 1B2 (5 µg/ml) was applied for 30 minutes. After washing four more times with PBS-BT, streptavidin-HRP (1:1000, Amersham) was added for 30 minutes and followed by another four washes. Samples were developed with the TMB 2-Component Microwell Peroxidase Substrate Kit (Kirkegaard and Perry Laboratories) and the reaction was halted with 2M $H_3PO_4$. Absorbance at 450 nm was measured and appropriate pre-dilution of samples ensured that only those data in the linear range and at similar signal intensities were considered in the analysis. The slope of the absorbance versus concentration curve was used to determine the relative amount of scTCR in each sample.

To confirm that the increases in 4-4-20 secretion determined by Western blotting also corresponded to increases in active 4-4-20 secretion, fluorescein-binding assays were performed. Fifteen µl of biotin-coated polystyrene bead suspension (FluoSpheres biotin-labeled microspheres, Invitrogen) was incubated with 600 µl of BlockAid blocking solution (Invitrogen) and sonicated for 5 minutes. Ten µl of a NeutrAvidin-fluorescein conjugate (5 mg/ml, Pierce) were then added and the mixture was incubated at 25° C. with shaking for 1 hour. After washing three times with 500 µl PBS-BSA, 10 µl of yeast supernatant containing the 4-4-20 scFv was applied to the fluorescein antigen-coated beads for 1 hour at 25° C. with shaking. The beads were collected by centrifugation and the liquid removed (depleted supernatant, inactive fraction). The beads were then resuspended in 20 µl of 100 mM fluorescein sodium salt (Sigma) for 30 minutes at 25° C.

with shaking. The excess free fluorescein competed with the fluorescein-labeled beads to release the bound 4-4-20 scFv (active fraction). Nonspecific binding of 4-4-20 scFv to the polystyrene beads was analyzed by following the same protocol but labeling the beads with NeutrAvidin (Pierce) which lacks the conjugated fluorescein. Samples of the original yeast supernatant, the depleted supernatant, and the active fraction were analyzed by quantitative Western blotting as described previously.

Results

Method for Screening Engineered Yeast for Increased Protein Production using Yeast Surface Display The quantitative level of protein display on the surface of yeast was used as a proxy screening variable for improved secretion strains. A library of yeast display strains was created by transforming the yeast surface display strain with a cDNA overexpression library (Liu, H., et al. 1992. Genetics 132:665-73). The resultant library contains engineered yeast strains that harbor two plasmids, each under the galactose-inducible GAL1-10 promoter. One plasmid contains an expression cassette that directs surface display of the heterologous protein of interest via fusion to the Aga2p mating protein that self assembles to the cell wall-anchored Aga1p protein. The second contains a yeast cDNA and mediates overexpression of an endogenous yeast protein. The yeast library was amplified in glucose to prevent growth rate and expression bias effects, and then was switched to induction medium containing galactose (FIG. 1). Upon induction, the protein of interest was displayed on the yeast surface, with the protein products of the different yeast cDNA plasmids harbored by each cell causing increased, decreased, or no change in protein display levels.

Because the protein of interest is displayed on the cell surface, it is accessible to epitope-specific antibodies. When followed by fluorescent secondary antibodies, the yeast cells were sorted on a single cell basis using flow cytometry to rapidly provide quantitative data corresponding to protein display levels. Thus, yeast cells exhibiting higher levels of fluorescence were isolated from the library population via fluorescence activated cell sorting (FACS) (FIG. 1). Subsequently, these desirable clones were amplified in glucose-based media and the cycle repeated to purify yeast clones that have elevated levels of surface display. Then, individual clones were tested for their level of protein display, and those containing cDNA that enhance display were sequenced for identification. Unique cDNA clones were then re-transformed into the parent display strain to confirm the phenotype and eliminate yeast mutation or epigenetic phenomena as causes of the observed display increases. Finally, the cDNA that improved surface display were tested for their effects on protein secretion. As described earlier, the selection strategy was designed based on previous findings that surface display levels of engineered scTCR proteins correlated well with secretion levels of these proteins (Shusta, E. V., et al. 2000. Nat Biotechnol 18:754-9; Shusta, E. V., et al. 1999. J Mol Biol 292:949-56). Since this relationship was crucial to the success of the selection strategy, we first tested whether or not the correlation between display level and secretion level holds when the yeast cell, rather than the protein, is engineered.

Testing the Correlation between Display and Secretion for Engineered Yeast

Figure 2:
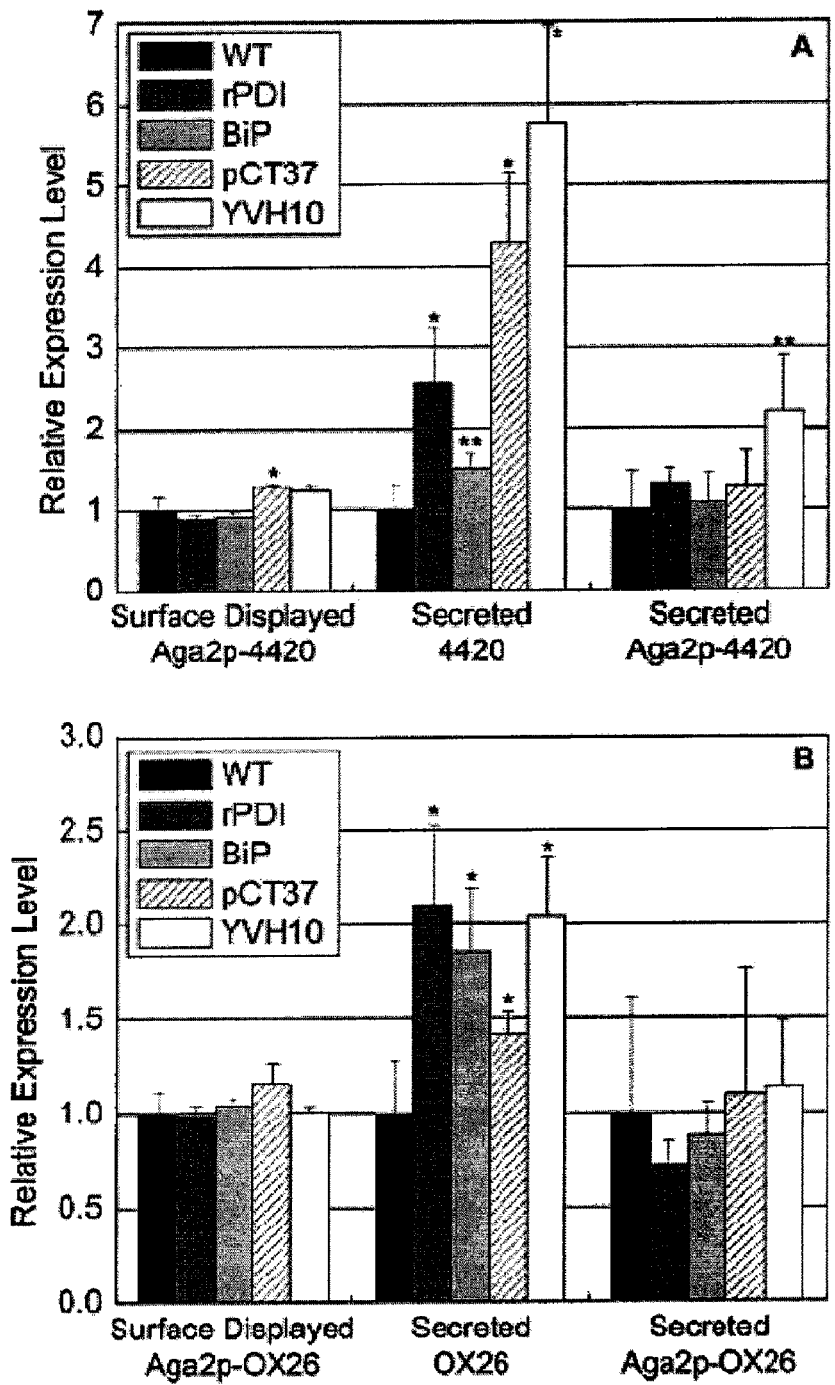
FIGS. 2A and B. Fusion to Aga2p eliminates the effects of folding assistants on secretion and display levels for the (A) 4-4-20 and (B) OX26 scFvs. Relative expression levels represent surface display levels of Aga2p-scFv measured by flow cytometry, secreted scFv levels measured by Western blotting, and secreted Aga2p-scFv levels measured by Western blotting. Because of variations in plasmid markers and the required yeast cell strains, each engineered cell was normalized to its appropriate wild-type background. The wild-type depicted in these plots was that corresponding to the wild-type system that yielded the highest standard error. Each data point represents triplicate display and secretion samples. Single (*) and double (**) asterisks represent $p<0.05$ and $p<0.07$, respectively. WT: wild-type, rPDI: rat PDI, BiP: yeast BiP/Kar2p, pCT37: plasmid-based yeast PDI overexpression, YVH10: integration-based yeast PDI overexpression.

Previous studies have revealed that certain yeast genes, such as heavy chain binding protein (BiP) and protein disulfide isomerase (PDI), when overexpressed result in increased secretion of proteins such as the anti-fluorescein 4-4-20 scFv (Shusta, E. V., et al. 1998. Nat Biotechnol 16:773-7) and the anti-transferrin receptor scFv (OX26) (Hackel, B. J., et al. 2006. Pharm Res 23:790-7). We therefore wished to test whether or not display levels of strains engineered to overexpress BiP and PDI would correlate with the observed increases in secreted levels. Since secretion of scFv is maximal in yeast when expression is induced at 20° C. (Huang, D., et al. 2006. Appl Environ Microbiol., Vol 72, 12:099-2240; van der Vaart, J. M., et al. 1995. J Bacteriol 177:3104-10; Zhang, W., et al. 2006. Biotechnol Prog 22:1090-5), and the goal of these screens was to maximize protein production, the presence or absence of a correlation was evaluated at this temperature. Yeast display and secretion strains were engineered to overexpress yeast BiP (Kar2p), yeast PDI (by plasmid, pCT37 and by integration, YVH10) and rat PDI, and display and secretion were induced at 20° C. Surface display data were obtained using flow cytometry and compared with secreted expression levels measured by Western blotting (FIG. 2). Both approaches employed the c-myc epitope tag present near the carboxy-terminus of each construct. Although secreted scFv was generally increased from yeast strains overexpressing BiP and PDI (1.4-2.1 fold for OX26 and 1.5-5.8 fold for 4-4-20), the surface display of these two proteins was unchanged by BiP and PDI overexpression (lone display increase was 4-4-20 with plasmid-based PDI overexpression 1.2-fold) (FIG. 2). Since the expected correlation between secretion and display of engineered yeast strains did not materialize in these small scale experiments, it was hypothesized that the presence of the Aga2p fusion partner required for scFv surface display negated the effects of the folding assistants by altering the secretory processing of the scFv.

Therefore, to test this hypothesis we analyzed the effect of the ER-resident folding assistants on secretion of the Aga2p-scFv fusion protein. Without high-level expression of the Aga1p cell wall anchor, Aga2p-scFv fusions are secreted from the cell rather than being displayed on the yeast surface (Huang, D., et al. 2005. Biotechnol Prog 21:349-57). In this way, the Aga2p-scFv constructs were secreted from the same strain as that used for secretion of the unfused scFv products, and secretion levels were analyzed by Western blotting. FIG. 2 indicates that the Aga2p-scFv fusions were not secreted at higher levels in the presence of BiP or PDI overexpression (lone exception 4-4-20 with integrated PDI, 2.2-fold). This contrasts dramatically with the effects that folding assistants have on the secretion of unfused scFv (FIG. 2), confirming that fusion to Aga2p obviates the positive effects that chaperones have on scFv processing. Therefore, Aga2p, and not scFv, determines display efficiency for these proteins.

Since the abovementioned experiments tested only BiP and PDI effects, it was possible that these folding assistants were simply special cases that were not responsive in a display format. Thus, we tested the effects of Aga2p fusion on the display responses for the entire yeast genome using the selection procedure outlined in FIG. 1 with 20° C. induction at step 3. Yeast overexpression libraries were screened for factors that increased the display of three different proteins, 4-4-20 and two single-chain T-cell receptors (7/15 and LWHI). The proteins were chosen because they have been previously produced in yeast as fully active proteins, and because they represent a range in display and secretion competence. The 4-4-20 scFv has secreted levels of 1 mg/L (Shusta, E. V., et al. 1998. Nat Biotechnol 16:773-7), while the 7/15 and LWHI scTCR are closely related mutants that differ in both display and secretion efficiency by approximately 20-fold (7/15, 0.1 mg/L versus LWHI, 2 mg/L) (Shusta, E. V., et al. 2000. Nat Biotechnol 18:754-9). Neither the 4-4-20 nor the scTCR screens yielded cDNA-dependent improvements in display levels after four rounds of sorting (data not shown). Combined with the data regarding the lack of BiP and PDI effects on display, the inability to recover improved clones from the genome-wide libraries of engineered yeast for three different proteins prompted us to conclude that unlike the correlation between display and secretion for an engineered protein, display effects generated by engineering the yeast cell were masked by fusion to Aga2p.

Screening of Yeast cDNA Library Under Selection Pressure

Since recovery of yeast proteins that enhance display was not possible under normal induction conditions (20° C.), a selection pressure was applied with the idea of making the fusion partner, rather than Aga2p, the dominant determinant of display efficiency. Of the four proteins studied here, the 7/15 scTCR is particularly poorly processed by the yeast cell at elevated temperatures (Shusta, E. V., et al. 2000. Nat Biotechnol 18:754-9). When surface display induction temperature was raised from 20° C. to 30° C. and 37° C., the surface display levels of scTCR dropped substantially (FIG. 3A), while the display of Aga2p alone was not dramatically affected (data not shown). Thus, it appeared that selection at elevated induction temperatures would allow isolation of yeast proteins that could overcome the defective processing and attenuated display of 7/15. In contrast, even though secretion of 4-4-20 and OX26 are decreased at elevated induction temperatures (Hackel, B. J., et al. 2006. Pharm Res 23:790-7; Shusta, E. V., et al. 1998. Nat Biotechnol 16:773-7), the display levels were not significantly altered by induction at elevated temperatures (data not shown), indicating that Aga2p was still serving as the determinant of display efficiency for these scFvs. Thus, we chose to use 7/15 as our bait to select cDNAs that recover the deficit in display at elevated temperatures. Yeast displaying 7/15 scTCR were transformed with the cDNA overexpression library and induced at either 30° C. or 37° C. and sorted for four rounds using the conformationally-sensitive 1B2 antibody that is a surrogate for the natural peptide-major histocompatibility complex and thus serves as a probe for display of active scTCR protein (Manning, T. C., et al. 1998. Immunity 8:413-25; Shusta, E. V., et al. 2000. Nat Biotechnol 18:754-9) (FIG. 1 with selection pressure at step 3). At the conclusion of the third sorting round, the mean cellular fluorescence level (scTCR display level) of the sorted pool was 2-fold higher than that of both the starting library and the wild-type display strain (FIGS. 3C and 3D), indicating the enrichment of clones with improved 7/15 display. After a final round of sorting to purify the improved clones, 29 total clones from the 30 and 37° C. sorts were tested and 28 of these led to 1.4- to 2.5-fold increased surface display at the elevated sort temperatures (data not shown). In contrast, the 28 clones were also tested at the 20° C. display induction temperature and only 12 showed higher expression ranging from 1.2- to 2.3-fold (data not shown). All individual clones were subjected to whole-cell PCR to recover the overexpressed cDNA, and those genes that possessed inserts of unique nucleotide lengths were sequenced for identification. The overexpressed genes leading to increased surface display at their respective elevated induction temperatures were identified as CCW12, CWP2, RPP0, SED1, and ERO1 (Table 2). With the lack of diversity in the pool sorted at 30° C. that contained mostly CCW12 clones, four clones from the earlier third round of sorting at 30° C. were tested as well. Only three of these clones showed increased 7/15 surface display when induced at 30° C., with two of the clones being identified as CCW12 while a third was homologous to RPL6A/B. CCW12, CWP2, and SED1 are all cell-wall associated proteins (Mrsa, V., et al. 1999. J Bacteriol 181:3076-86; Shimoi, H., et al. 1998. J Bacteriol 180:3381-7; van der Vaart, J. M., et al. 1995. J Bacteriol 177:3104-10), while RPP0 and RPL6A/B are constituents of the ribosome (Newton, C. H., et al. 1990. J Bacteriol 172:579-88; Planta, R. J., et al. 1998. Yeast 14:471-7). ERO1 localizes to the endoplasmic reticulum (ER) and provides PDI with oxidizing equivalents for disulfide bond rearrangement (Pollard, M. G., et al. 1998. Mol Cell 1:171-82; Tu, B. P., et al. 2000. Science 290:1571-4).

Figure 3:
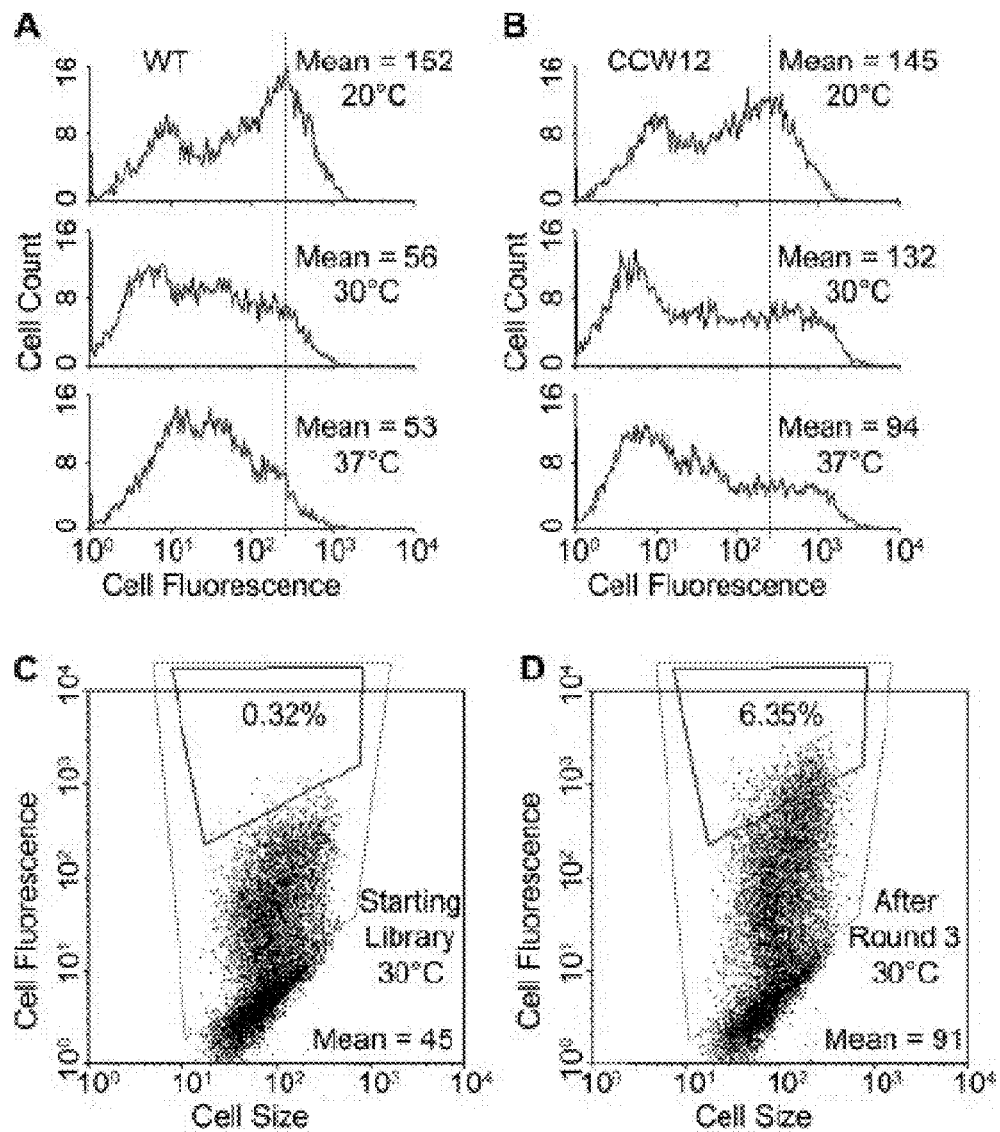
FIG. 3A-D. Identification of yeast genes that increase 7/15 scTCR surface display by using elevated induction temperatures. (A) Histograms depicting the effects of increasing induction temperature (Manning, T. C., et al. 1998. Immunity 8:413-25, 30, 37° C.) on 7/15 display. (B) Histograms depicting the effects of CCW12 overexpression on 7/15 display at different induction temperatures (Manning, T. C., et al. 1998. Immunity 8:413-25, 30, 37° C.). (C) Flow cytometric dot plot of 7/15-displaying yeast that harbor the cDNA library (30° C. sort). The yeast population that displays active 7/15 is enclosed in the large rectangle, while a sample sort gate is also shown at 0.32 percent of the total population. (D) The population after the third round of 30° C. sorting shows enrichment of clones having higher display levels with the mean of the positive population doubling and the percent of the total population contained in the original sort gate increasing by almost 20-fold. Reported are geometric means of the population of yeast that were displaying protein on the cell surface. This approach makes use of a second epitope tag that allows exclusion of non-displaying yeast from the analysis (negative population can be seen in the histograms as a peak with low mean fluorescence of ~6-8). All flow cytometry data was obtained via antibody labeling with the 1B2 activity probe and represents 10,000 yeast cells. Histograms are representative of triplicate samples, and the vertical lines are inserted to facilitate comparison of the fluorescence of the positive display peak.
Figure 4:
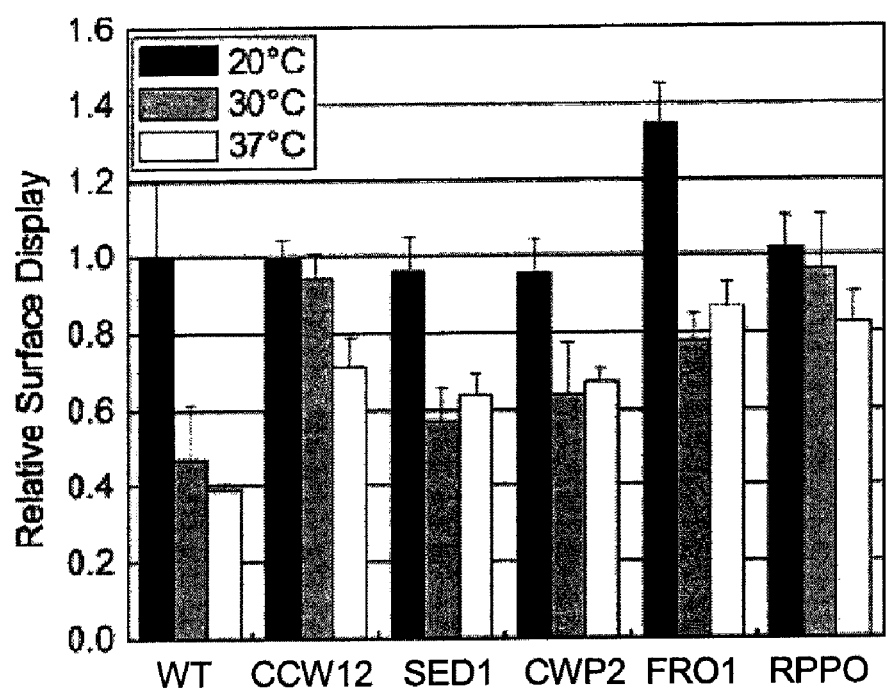
FIG. 4. Effects of overexpressed cDNA on surface display levels of 7/15 scTCR at the various induction temperatures. Samples were analyzed via flow cytometry in the same manner as in FIG. 3. Data represent triplicate cultures whose display levels are normalized to the WT at 20° C. Data representing only the positive displaying population were analyzed. The main cause for the appearance of negative display peaks in yeast surface display experiments has been determined to be plasmid stability (28). In no case, did the overexpressed cDNA alter the percentage of displaying yeast in the population, indicating that the cDNA did not affect plasmid stability in the displaying strains.

Effects of Display Enhancers on scTCR Display at Normal and Elevated Temperatures Each unique overexpression plasmid listed in Table 2 was recovered from the corresponding yeast clone to confirm the cDNA-based influences on display phenotype. The parent yeast surface display strain (AWY100) was transformed with both the pCT-7/15 display vector and the recovered overexpression plasmids, and display at each induction temperature evaluated by flow cytometry (FIGS. 3A and 3B, FIG. 4). The mean display level of each engineered yeast strain was normalized to that of the wild-type population at 20° C. for comparison purposes. It was found that all genes show statistically significant increases in display levels of active protein for at least one of the elevated induction temperatures when compared to the wild-type population at the same temperature (1.2-2.2 fold, $p<0.05$). Most exhibited improvements in display at both 30° C. and 37° C. regardless of what sort they were identified in. The lone exception was RPL6A/B, as it did not prove to increase 7/15 display at any temperature tested and behaved exactly like the wild-type (data not shown). Furthermore, at the 30° C., CCW12 and RPP0 overexpression recovers 7/15 surface display to the same level as the wild-type at 20° C. Only ERO1 overexpression resulted in a statistically significant increase in 7/15 display at 20° C. ($p<0.06$). Taken together, these results indicate that a 20° C. sort would not have identified the majority of the display enhancers, as also indicated by our failed screens at 20° C. with 4-4-20, 7/15 and LWHI. Since the screen involved manipulation of cell-wall proteins by fusion to the Aga2p protein and surface tethering via the Aga1p protein, CCW12, CWP2, and SED1 could either play a beneficial role in increasing surface display by Aga1p/Aga2p modulation or by improving scTCR processing through the secretory pathway. To test which of these possibilities was most likely, the Aga2p was displayed alone without any scTCR fusion. There was no change in Aga2p display in any of the engineered yeast strains at any of the temperatures tested (data not shown) indicating that the observed increases in display in the presence of overexpressed cDNAs were scTCR-dependent. This result suggested that the yeast proteins recovered in our screen therefore had potential to increase heterologous protein secretion in addition to improving display levels. Therefore, we opted to test each of the recovered yeast proteins for their effects on the secretion of four heterologous proteins, and in doing so, tested the generality of our hypothesis that display and secretion levels would be coordinately regulated as a result of selection pressure.

Effects of Display Enhancers on the Secretion of Four Heterologous Proteins

Figure 5:
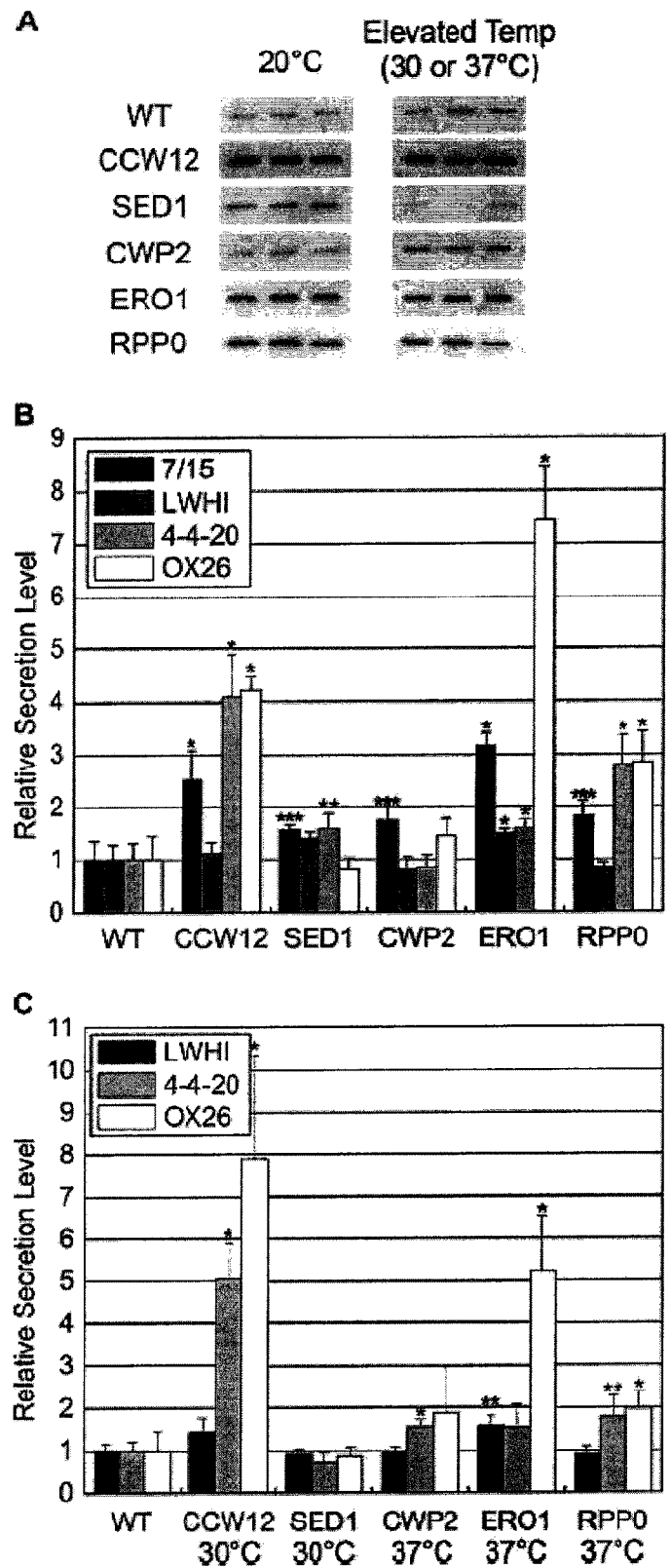
FIG. 5A-C. Effects of overexpressed cDNA on secretion levels of scTCRs and scFvs. (A) Representative Western blotting data for 4-4-20 scFv secretion experiments. Triplicate supernatants derived from independent transformants were used to generate the Western blotting signals. Within each temperature condition, the data shown are from the same time point of exposure and can therefore be directly compared. However, these only serve as qualitative comparisons, while quantitative values and associated statistical significance can be found in Panels B and C (see Materials and Methods for quantitation details). (B) Secretion yields after induction at 20° C. (C) Secretion yields after elevated temperature induction. As indicated in Panel C, each cDNA overexpression strain was evaluated at the elevated induction temperature at which it was selected. 7/15 secretion levels were detected by quantitative ELISA while all other protein levels were measured by quantitative Western blotting, as depicted for 4-4-20 in panel A. Activity assays confirmed that increased secretion of 4-4-20 and LWHI expression detected via Western blotting was representative of active protein levels. Single (*) and double () asterisks represent $p<0.05$ and $p<0.1$, respectively, and were reproducibly significant over three independent experiments. Triple asterisks (*) indicate data that were statistically significant ($p<0.05$) for the experiment presented, but were not reproducibly significant over multiple experiments. These *** conditions were therefore reported as incapable of increasing secretion levels. Triplicate independent transformants were evaluated for each protein-cDNA combination, and all data were normalized to the WT at the corresponding temperature.

Since 20° C. has been shown to be the optimal induction temperature for the secretion of many scFv and scTCR fragments (Hackel, B. J., et al. 2006. Pharm Res 23:790-7; Shusta, E. V., et al. 1998. Nat Biotechnol 16:773-7), the 5 yeast proteins were first tested for their effects on 20° C. secretion of 7/15 scTCR, LWHI scTCR, 4-4-20 scFv, and OX26 scFv (FIGS. 5A and 5B). Secretion levels of 7/15 scTCR were determined by a high sensitivity ELISA utilizing a tetra-His capture antibody (intact carboxy-terminus) and biotinylated 1B2 (active) as a means of detection. Thus, this assay serves as a direct readout of full-length, active protein. At 20° C., overexpression of CCW12 and ERO1 increased secretion of active 7/15 scTCR protein by 2.5- and 3.2-fold, respectively (FIG. 5B). In contrast, SED1, CWP2, and RPP0 did not reproducibly increase 7/15 secretion titers. Similar to the case with 7/15, 4-4-20 and OX26 scFvs were secreted at higher levels (from 1.6- to 7.4-fold), as assessed by Western blotting, when CCW12 and ERO1 were overexpressed, indicating a generality in the secretion enhancing effects of these yeast proteins (FIGS. 5A and 5B). Overexpression of RPP0 also enhanced the secretion levels of these two scFv (2.8-fold). To confirm that scFv secretion increases indicated by Western blotting represented increased yields of active protein, anti-fluorescein scFv 4-4-20 activity assays were performed (See Materials and Methods for details) and indicated that the amount of scFv that undergoes a reversible, fluorescein-dependent binding is increased by 4.7-fold in the presence of CCW12 overexpression (compared with 4.1-fold determined by Western blotting). Protein-specific effects were observed as the secretion of LWHI is only affected in the presence of ERO1 overexpression which leads to a marginal increase in secretion as assessed by Western blotting (1.6-fold). In addition, ERO1-mediated increases in LWHI secretion were confirmed by ELISA activity assay (1.8-fold) to ensure that Western blotting data were indicative of the increases in secretion levels of active protein. As protein-specific effects suggest, general cell-based phenomena induced by the cDNA were not responsible for the observed increases in secretion. In particular, the cytoplasm-resident glyceraldehyde-3-phosphate dehydrogenase (G3PDH) protein could not be detected in the 4-4-20 supernatants with or without CCW12 overexpressed (data not shown). This finding indicated that cell lysis was not responsible for the increased amount of active protein accumulated in the supernatant.

Since all of the identified yeast genes elicited their most significant effects on surface display at the elevated induction temperatures, secretion using 30° and 37° C. induction was also investigated to determine induction temperature effects on secretion levels. Given the sensitivity of 7/15 display as a function of temperature even though the scTCR is expressed as a fusion to Aga2p, it was not surprising that secreted unfused 7/15 scTCR was not detectable after 30° or 37° C. induction even in the presence of the overexpressed genes (data not shown). Therefore, we also tested the effects of the overexpressed cDNAs and induction temperature on the more stable LWHI scTCR, along with 4-4-40 and OX26 scFvs (FIG. 5C). The first finding was that the elevated temperatures had the general effect of lessening the impact of overexpressed cDNA both by decreasing the magnitude of improvement and by causing fewer cDNAs to have impact (compare FIGS. 5B and 5C). As described above, activity tests indicated that the increases in secretion reported at the elevated temperatures again represented increases in active protein (4-4-20 with CCW12 at 30° C., and LWHI with ERO1 at 37° C.). The final two cDNAs tested, SED1 (4-4-20 at 20° C.) and CWP2 (4-4-20 at 37° C.), had the most limited overall effects on secretion and only modestly boosted secretion for a single scFv under discrete conditions.

Finally, the absolute secretion levels at the different induction temperatures were compared. As observed previously (Hackel, B. J., et al. 2006. Pharm Res 23:790-7;, Shusta, E. V., et al. 1998. Nat Biotechnol 16:773-7), the absolute secretion levels of the scFvs in the wild-type system were not increased by raising the induction temperature from 20° C. to 30° C. or 37° C. In the presence of cDNA, the only elevated temperature conditions whose absolute scFv production levels exceeded that seen for the same system at 20° C. were 4-4-20 with CWP2 at 37° C. (1.6-fold increase). In contrast, the optimal secretion temperature for the stable LWHI scTCR in the wild-type system was 30° C. (2-fold increase over that seen at 20° C.), and only in the presence of ERO1 were the effects of cDNA noticeable at increased temperature (1.6-fold at 37° C.). Thus, as a general rule, the 20° C. system with overexpressed cDNA (CCW12, ERO1, or RPP0) most often yielded the maximum amount of secreted protein.

Discussion

This study described the mining of a library of engineered yeast strains modified by overexpression of endogenous yeast proteins. It was discovered that although yeast surface display allowed rapid quantitative sorting of the engineered strains, the Aga2p tether masked the effects that the overexpressed yeast proteins had on the scFv or scTCR fusion partner. However, one of the proteins (7/15 scTCR) was particularly sensitive to induction temperature. Thus, under the influence of an elevated temperature that decreased the efficiency of intracellular processing, several yeast strains that promoted increased display and secretion were isolated. The increases were mediated by overexpression of translational components (RPP0), ER-resident folding assistants (ERO1), and cell wall proteins (SED1, CCW12, CWP2), few of which would likely have been predicted a priori. The increases in heterologous protein secretion were not limited to the screened scTCR, but were also generalizable to additional scTCR and scFv proteins.

Although secreted protein and Aga2p fusion protein destined for display on the cell surface both traverse the same secretory compartments, our observations indicated that the association with the cellular folding machinery, such as BiP and PDI, differed substantially. In particular, increasing the expression levels of the ER-resident BiP and/or PDI had already proven successful in increasing secretion of scFv and scTCR from S. cerevisiae (this work and references (Hackel, B. J., et al. 2006. Pharm Res 23:790-7; Shusta, E. V., et al. 2000. Nat Biotechnol 18:754-9; Shusta, E. V., et al. 1998. Nat Biotechnol 16:773-7)). However, BiP and PDI overexpression had no effect on surface display levels. In addition, although an scFv and two scTCR that differ 20-fold in secretion efficiency were put through the initial selection strategy without selection pressure, no overexpressed yeast proteins that could increase display levels were identified. Thus, it appeared that fusion to the Aga2p display scaffold enabled the scFv to bypass the intracellular bottleneck normally encountered by unfused scFv. In addition, even when scFv display was induced at elevated temperatures that normally diminish secretion titers (Hackel, B. J., et al. 2006. Pharm Res 23:790-7; Shusta, E. V., et al. 1998. Nat Biotechnol 16:773-7), the display levels were not affected, again indicating that Aga2p could dominate the display efficiency of its scFv fusion partner. The consequence of these findings is that screens for engineered yeast cannot be performed under conditions where Aga2p dominates display efficiency.

Thus, to overcome the dominant effects of Aga2p and allow the yeast strain engineering approach to identify yeast proteins that can enhance display and secretion, we employed an scTCR protein whose display levels, unlike the scFv, were particularly responsive to a selection pressure of elevated induction temperature. In this way, five yeast genes that restore or increase display levels of active protein were identified. Although the five yeast genes increased display of the low stability 7/15 scTCR at the elevated temperatures, only ERO1 overexpression increased display levels at 20° C. (1.4-fold increase), again suggesting that the selection pressure was required to select CCW12, RPP0, SED1, and CWP2 from the yeast library due to Aga2p masking effects. Therefore, although it would be ideal to use this system to screen engineered yeast libraries for any heterologous protein of interest, the protein of interest must be responsive to a selection pressure such as elevated induction temperature for the display-based screen to be successful. However, display-based screening with a single protein substrate allowed the identification of five yeast proteins, several of which can serve as fairly generalizable secretion assistants as discussed below.

Although the five yeast genes were selected at higher temperatures, all except CWP2 promoted increased secretion of at least one protein at 20° C., and 20° C. proved optimal for the maximum secretion levels. The two scFv tested behaved similarly to the 7/15 scTCR in that CCW12 and ERO1 could enhance secretion, albeit to differing extents. However, unlike 7/15, the scFvs exhibited increased secretion levels in response to RPP0 overexpression. In contrast to these three proteins, the ultrastable LWHI scTCR did not respond to any of the overexpressed yeast genes other than showing modest increases with ERO1 overexpression. Taken together, the temperature-dependent display enhancers (CCW12, CWP2, SED1, RPP0) seem to facilitate secretion of the lower expression/stability proteins, while secretion of the LWHI protein was unaffected. On the other hand, the lone 20° C. display enhancer, ERO1, yielded statistically significant increases in secretion for all proteins tested indicating that the most general solutions would be those selected under conditions of 20° C. induction. Unfortunately, as discussed above, the presence of Aga2p prevents such direct selections from being successful.

Two of the isolated display enhancers, Ero1p and Rpp0p, are known to function directly in the protein synthesis and folding process and were therefore expected to enhance protein secretion. The Ero1p protein is essential for yeast viability and functions in delivering oxidizing equivalents to folding disulfide-containing proteins through PDI (Frand, A. R., et al. 1998. Mol Cell 1:161-70; Pollard, M. G., et al. 1998. Mol Cell 1:171-82; Tu, B. P., et al. 2000. Science 290:1571-4). ERO1 is induced by the unfolded protein response and loss of Ero1p results in accumulation of reduced protein in the ER (Frand, A. R., et al. 1998. Mol Cell 1:161-70, Pollard, M. G., et al. 1998. Mol Cell 1:171-82). Therefore, since each of the heterologous proteins investigated contains two disulfide bonds, overexpression of Ero1p likely assists in the formation of these disulfide bonds and promotes exit from the ER. For example, overexpression of *Kluveromyces lactis* ERO1 has led to increased secretion of disulfide-bonded human serum albumin, but not disulfide-free interleukin 1-B (Lodi, T., et al. 2005. Appl Environ Microbiol 71:4359-63). The P0 protein (Rpp0p) is one of a set of proteins that assemble at the stalk of the large ribosomal subunit in yeast (Mitsui, K., et al. 1988. Nucleic Acids Res 16:3573; Santos, C., et al. 1994. J Biol Chem 269:15689-96), and excess Rpp0p is not normally observed (Santos, C., et al. 1994. J Biol Chem 269:15689-96). Thus, it may be possible that under conditions of heterologous protein overexpression, the Rpp0p protein may be a limiting component in the ribosomal assembly, and this deficiency in protein translation capacity may be alleviated by overexpression of the Rpp0p protein. Alternatively, Rpp0p may be functioning indirectly as overexpressed Rpp0p has been implicated in alleviating prion formation in yeast by increasing the activity of promoters containing heat shock elements that drive expression of many chaperones and foldases ( Kryndushkin, D. S., et al. 2002. J Biol Chem 277: 23702-8).

We initially hypothesized that several of the genes recovered in the library screen, namely CCW12, CWP2 and SED1 might not increase secretion of the unfused 7/15 scTCR, as these genes have cellular functions related to the yeast cell wall. Since the flow cytometry selection process required surface display involving the Aga1p and Aga2p cell wall proteins, the recovered clones could have been the result of "you get what you select for", and yeast proteins that facilitate Aga1p and/or Aga2p assembly and processing, rather than scTCR processing, could have been selected. However, none of the cell wall proteins, when overexpressed, affected the display of Aga2p lacking the scTCR fusion partner. Thus, it appeared that the cell wall proteins were regulating surface display in a scTCR-dependent manner, and may have had a general influence on the secretory processing of scTCR. Indeed, overexpression of the cell wall genes increased both the surface display of 7/15 (CCW12, CWP2, SED1) and the secretion of 7/15 (CCW12). ScFv secretion was also elevated by CCW12 overexpression, and to a lesser extent by CWP2 and SED1. In contrast, the LWHI scTCR was unaffected by cell wall protein expression indicating protein-specific effects, and not a general change in cell physiology.

Each of the cell wall proteins is covalently linked to the cell wall glycan layer after processing as a GPI-anchored precursor (Mrsa, V., et al. 1999. J Bacteriol 181:3076-86; Oender, K., et al. 2003. Yeast 20:281-94; van der Vaart, J. M., et al. 1995. J Bacteriol 177:3104-10). The proteins have generally been implicated in providing cell wall stability and resistance to stresses. For example, CCW12 deletion or overexpression increases the sensitivity to known cell wall perturbants, calcofluor white and congo red (Mrsa, V., 1999. J Bacteriol 181:3076-86), deletion of SED1 made stationary phase cells more sensitive to zymolase treatment (Shimoi, H., et al. 1998. J Bacteriol 180:3381-7), and deletion of CWP2, like CCW12, increased sensitivity to calcofluor white and congo red while also increasing the sensitivity of exponentially growing cells to zymolase treatment (van der Vaart, J. M., et al. 1995. J Bacteriol 177:3104-10). Thus, the stresses imposed by heterologous protein display and secretion may be diminished by overexpression of cell wall proteins. Although further study will be required to elucidate the mechanism whereby the cell wall proteins assist secretion and display, the results of this study clearly point to the cell wall as a novel target for secretion improvement.

TABLE 1

| | Strains and plasmids. | | |
|---|---|---|---|
| Yeast Strain/Plasmid | Genotype/Gene | Display or Secretion | Reference |
| EBY100 | MATa AGA1::GAL1-AGA1::URA3 ura3-52 trp1 leu2Δ1 his3Δ200 pep4::HIS3 prb1Δ1.6R can1 GAL | Display | Boder, E. T., and K. D. Wittrup. 1997. Nat Biotechnol 15: 553-7 |
| AWY100 | MATa AGA1::GAL1-AGA1::LEU2 ura3-52 trp1 leu2Δ1 his3Δ200 pep4::HIS3 prb1Δ1.6R can1 GAL | Display | This study |

TABLE 1-continued

Strains and plasmids.

| Yeast Strain/Plasmid | Genotype/Gene | Display or Secretion | Reference |
|---|---|---|---|
| AWY101 | MATα AGA1::GAL1-AGA1::URA3 PDI1::GAPDH-PDI1::LEU2 ura3-52 trp1 leu2Δ1 his3Δ200 pep4::HIS3 prb1Δ1.6R can1 GAL | Display | This study |
| AWY102 | MATα AGA1::GAL1-AGA1::URA3 ura3-52 trp1 leu2Δ1 his3Δ200 pep4::HIS3 prb1Δ1.6R can1 GAL | Display | This study |
| BJ5464 | MATα ura3-52 trp1 leu2Δ1 his3Δ200 pep4::HIS3 prb1Δ1.6R can1 GAL | Secretion | Jones, E. W. 2002. Methods Enzymol 351: 127-50 |
| YVH10 | MATα PDI1::GAPDH-PDI1::LEU2 ura3-52 trp1 leu2Δ1 his3Δ200 pep4::HIS3 prb1Δ1.6R can1 GAL | Secretion | Robinson, A. S., V. Hines, and K. D. Wittrup. 1994. Biotechnology (NY) 12: 381-4 |
| pCT-4420His6 | Aga2p-4420 | Both | This study |
| pCT-OX26 | Aga2p-OX26 | Both | This study |
| pCT-7/15 | Aga2p-7/15 | Display | Kieke, M. C., et al. 1999. Proc Natl Acad Sci U S A 96: 5651-6 |
| pCT-LWHI | Aga2-LWHI | Display | Shusta, E. V., et al. 2000. Nat Biotechnol 18: 754-9 |
| pRS316-4420His6 | 4420 | Secretion | This study |
| pRS-GALT7/15 | 7/15 | Secretion | Shusta, E. V., et al. 1999. J Mol Biol 292: 949-56 |
| pRS-GALTLWHI | LWHI | Secretion | Shusta, E. V., et al. 2000. Nat Biotechnol 18: 754-9 |
| PRS316-GALOX26 | OX26 | Secretion | Hackel, B. J., et al. 2006. Pharm Res 23: 790-7 |
| pGAL-KAR2LEU | BiP (Kar2p) | Both | Robinson, A. S., et al. 1996. J Biol Chem 271: 10017-22 |
| pMAL5.1 | Rat PDI | Both | Laboissiere, M. C., et al. 1995. J Biol Chem 270: 28006-9 |
| pCT37 | Yeast PDI | Both | Tachibana, C., and T. H. Stevens. 1992. Mol Cell Biol 12: 4601-11 |

TABLE 2

Yeast cDNAs that enhance scTCR display.

| Gene | Screen Temperature | Frequency |
|---|---|---|
| CCW12 | 30° C. | 17 |
| SED1 | 30° C. | 1 |
| CWP2 | 37° C. | 3 |
| ERO1 | 37° C. | 4 |
| RPP0 | 37° C. | 3 |

Example II

Enhanced Secretion of Heterologous Proteins from Yeast by Overexpression of Ribosomal Subunit RPP0

In General

Previously, we have shown that single-gene overexpression of five yeast genes (CCW12, CWP2, ERO1, RPP0, and SED1) promoted increased secretion levels of several single-chain antibody fragments and single-chain T-cell receptors from *Saccharomyces cerevisiae* (Wentz, A. E.; Shusta, E. V., Appl Environ Microbiol 2007, 73, (4), 1189-98, see Example I). In this study, several proteins possessing different protein folds were secreted from yeast overexpressing each of the five genes to determine the generality of the secretion enhancers. Only one gene encoding a ribosomal subunit (RPP0) enhanced secretion levels for multiple proteins: a single-chain antibody (the 4-4-20 anti-fluorescein scFv) and green fluorescent protein (GFP). Protein induction time-course experiments revealed secretion increases with RPP0 overexpression for 4-4-20 as early as 40 hours post-induction. Effects on GFP secretion levels were not evident until late induction times where overexpression of RPP0 limited post-secretion protein loss, but absolute yields did not exceed those observed at earlier induction times. The effects of RPP0 overexpression on secreted protein yields did not appear to directly involve ribosome function, but instead RPP0 overexpression indirectly regulated acidification of the yeast medium by preventing upregulation of the yeast plasma membrane $H^+$-ATPase gene, PMA1. Combining RPP0 overexpression with nutrient supplementation stimulated additional protein secretion for the 4-4-20 scFv with higher per cell secretion that corresponded to 6-fold increases in volumetric yield.

Introduction

The yeast *Saccharomyces cerevisiae* has been commonly utilized for the secretion of heterologous proteins, yet foreign protein yields in yeast are often low. To help address this shortcoming, a screen for potential secretion enhancers was performed and five yeast genes were recovered (CCW12, CWP2, ERO1, RPP0, and SED1) that when overexpressed resulted in increased surface display and secretion of heterologous proteins from yeast (Wentz, A. E.; Shusta, E. V. Appl Environ Microbiol. 2007, 73, (4), 1189-98). Interestingly, these five genes localize to several different regions within the yeast cell and vary in function. The protein product for ERO1 is the only known participant of the secretory process and localizes to the endoplasmic reticulum (ER) where it provides oxidizing equivalents to protein disulfide isomerase (PDI) for disulfide bond rearrangement (Frand, A. R. and Kaiser, C. A., Mol Cell. 1998, 1, (2), 161-70; Lodi, T., et al., Appl Environ Microbiol. 2005. 71(8) 4359-63; Pollard, M. G.; et al., Mol Cell 1998. 1(2)171-82; Tu, B. P.; Ho-Schleyer, S. C.; et al., S., Science. 2000. 290(5496)1571-4). RPP0 encodes the P0 protein that is essential for ribosome activity and along with the P1 and P2 proteins forms the stalk of the large ribosomal subunit (Mitsui, K. and Tsurugi, K. Nucleic Acids Res. 1988.16(8)3573; Santos, C. and Ballesta, J. P. J Biol Chem. 1994. 269(22)15689-96; Krokowski, D.; et al. Biochim Biophys Acta. 2005. 1724(1-2)59-70.), while CCW12, CWP2, and SED1 each encode a cell wall-associated protein and function to stabilize the cell wall and provide resistance to various external stresses (Mrsa, V. et al. J Bacteriol. 1999. 181(10)3076-86; Oender, K.; et al. Yeast. 2003. 20(4)281-94; van der Vaart, J. M., et al. J Bacteriol. 1995. 177(11) 3104-10; Shimoi, H.; et al. J Bacteriol. 1998.180(13)3381-7). Results from the previous study revealed single-gene overexpression of the five genes provided significant enhancements in secretion of several single chain antibody fragment (scFv) and single chain T-cell receptor (scTCR) proteins containing similar immunoglobulin folds but having substantially different secretion titers (0.05 to 2 mg/L).

Example II focuses on the effects of overexpression of the five genes on enhancing secretion of multiple heterologous proteins containing different folding motifs. Different protein folds were evaluated as substantial evidence indicates that when dealing with the effects of overexpressed genes on secretion, many outcomes are protein-specific. For example, overexpression of PDI increased the yields of 4-4-20 by 6-fold (Wentz, A. E. and Shusta, E. V., Appl Environ Microbiol. 2007. 73(4)1189-98) and human platelet derived growth factor by 10-fold (Robinson, A. S. et al. Biotechnology (NY). 1994. 12, (4), 381-4)., yet failed to produce higher levels of an scFv fusion protein (Wentz, A. E. and Shusta, E. V. Appl Environ Microbiol. 2007. 73(4), 1189-98) or human granulocyte colony stimulating factor ( Robinson, A. S.; et al. Biotechnology (NY). 1994. 12(4) 381-4). Thus in an effort to evaluate the generality of the five aforementioned secretion enhancers, the heterologous proteins analyzed in this example include the 4-4-20 scFv containing the β-sandwich immunoglobulin fold, green fluorescent protein (GFP) and bovine pancreatic trypsin inhibitor (BPTI). GFP consists of 238 amino acids that form a β-barrel structure surrounding the fluorophore (Yang, F.,et al. Nat Biotechnol. 1996. 14(10) 1246-51). GFP is also a useful model protein to study the yeast secretory pathway because active GFP is readily detected and visualized in the yeast cell (Cormack, B. Curr Opin Microbiol. 1998. 1(4)406-10; Huang, D. and Shusta, E. V. Biotechnol Prog. 2005. 21(2)349-57). BPTI is a small (58 amino acids), highly stable, single-domain protein containing three disulfide bonds and consisting of both an α helix and β sheets (Goldenberg, D. P. Trends Biochem Sci. 1992. 17(7) 257-61; van Mierlo, C., et al. J Mol Biol. 1991. 222(2)373-90). Results indicated that RPP0 was the only overexpressed gene that provided enhanced secretion of multiple proteins, and we therefore further investigated its mode of action.

Materials and Methods

Yeast Strains, Plasmids, and Media

All secretion assays were performed with fresh transformants in the S. cerevisiae strains BJ5464 (MATα ura3-52 trp1 leu2Δ1 his3Δ200 pep4::HIS3 prb1Δ1.6R can1 GAL) (Jones, E. W. Methods Enzymol. 2002. 351, 127-50.) or BJ5464 with a HAC1 gene deletion (denoted as the hac1Δ strain) (MATα hac1Δ::kan$^r$ ura3-52 trp1 leu2Δ1 his3Δ200 pep4::HIS3 prb1Δ1.6R can1 GAL). Cells were transformed using the lithium acetate method (Parekh, R., et al. Protein Expr Purif. 1995. 6(4)537-45) with a plasmid encoding the heterologous protein to be secreted (pRS314-4420His6 (1), pYC-(G)-BPTI (21), or pRS314-GFP) and a pRS316-GAL1-cDNA plasmid containing the yeast cDNA of interest (CCW12, CWP2, ERO1, RPP0, or SED1). All pRS316-GAL1-cDNA plasmids were isolated during a previous study (Wentz, A. E. and Shusta, E. V. Appl Environ Microbiol. 2007. 73(4)1189-98) and cDNA expression is controlled by the galactose-inducible GAL1-10 promoter. Secretion plasmids for the heterologous proteins contain the 4-4-20, BPTI, or GFP genes also under the control of the GAL1-10 promoter. pRS314-GFP was created by subcloning GFP from pRS316-GFP (Huang, D. and Shusta, E. V. Biotechnol Prog. 2005. 21(2) 349-57) into pRS-314 (Sikorski, R. S. and Hieter, P. Genetics. 1989. 122(1)19-27) using KpnI/SacI restriction sites that allow shuttling of the entire expression cassette. Wild-type strains contained a null pRS-316 plasmid (Sikorski, R. S. and Hieter, P. Genetics. 1989. 122(1)19-27) in place of the pRS316-GAL1-cDNA construct. Negative control strains were transformed with both pRS-314 and pRS-316. Yeast were grown in SD-CAA minimal medium (2% dextrose, 0.67% yeast nitrogen base, 0.5% Casamino acids) buffered at pH 6.0 with 50 mM sodium phosphate. Induction of protein secretion and cDNA overexpression was performed in either 1× (50 mM phosphate) or 2× (100 mM phosphate) buffered SG-CAA medium supplemented with 1 mg/mL bovine serum albumin (BSA) as a carrier and having dextrose replaced with 2% galactose.

Heterologous Protein Secretion

Cultures were inoculated into SD-CAA medium and grown overnight at 30° C. prior to dilution to a uniform $OD_{600}$ of 0.1 and regrowth for 3 days to an $OD_{600}$ between 8 and 10. Protein expression was then induced by switching to either the 1× or 2× media and placing the cultures at 20° C. for 3 days. All experiments were performed in 3 mL volumes. Nutrient supplementation involved adding 200 μL of a 10× solution containing 6.7% yeast nitrogen base and 5% Casamino acids to yeast cultures at both 24 and 48 hours post-induction. Time-course experiments were sampled over the 72-hour induction period by removing 100 μL of the culture for measurement of cell density ($OD_{600nm}$), analysis of intracellular content, and determination of secretion yield. Yeast cells and supernatants were stored at −20° C. when necessary.

Protein Quantification

Protein levels were measured with sodium dodecyl sulfate polyacrylamide gel electrophoresis (SDS-PAGE) and quantitative Western blotting. The cell-free GFP and 4-4-20 supernatants were resolved on a 12.5% polyacrylamide-SDS gel and transferred to nitrocellulose membranes. The membranes were probed with the 9E10 anti-c-myc antibody (1:3,000; Covance, Berkeley, Calif.) followed by a horseradish peroxidase (HRP)-conjugated anti-mouse secondary antibody (1:2, 000; Sigma, St. Louis, Mo.). BPTI levels were measured using an activity assay based on trypsin inhibition. The protocol was similar to that reported elsewhere (21). Briefly, 0.5 mL of various dilutions of BPTI supernatant in SG medium were added to a cuvette containing 2.5 mL buffer (15 mM CaCl$_2$, 0.2 M triethanolamine, buffered with citrate to pH 7.8) and 50 µL of a 0.4 mg/mL solution of trypsin (Worthington Biochemical, Lakewood, N.J.). Samples were incubated for 30 minutes at 30° C. to allow BPTI/trypsin binding prior to addition of 150 µL of a 24 mg/mL solution of the trypsin substrate L-BAPA (N☐-Benzoyl-D,L-arginine 4-nitroanilide hydrochloride) (Sigma) dissolved in dimethyl sulfoxide (DMSO). The reaction rate at 405 nm (increase in absorbance) was measured for 3 minutes. The x-intercept from a plot of the reaction rate versus amount of BPTI added provides the amount of BPTI required to inhibit all of the added trypsin, assuming a 1:1 molecular ratio of trypsin to BPTI, thus providing the absolute amount of BPTI present in the supernatant.

For intracellular protein analysis, cells were lysed with a 50 µL solution containing 42 µL CelLytic-Y™ (Sigma), 7 µL of a 7× Complete Mini Protease Inhibitor Cocktail (Roche, Indianapolis, Ind.) and 1 µL of a 0.1 M phenylmethanesulphonylfluoride (PMSF) (Roche) solution (PMSF dissolved in isopropanol). Rpp0p intracellular expression levels over the 72-hour induction time course were measured for both WT and RPP0-overexpressing cultures via SDS-PAGE and probing of the nitrocellulose membrane with the 3BH5 antibody (1:10, kind gift of Juan P. G. Ballesta) followed by anti-mouse HRP (discussed above). Total intracellular GFP levels were determined using Western blotting of cell lysates as described directly above for GFP supernatants. Intracellular active GFP levels were analyzed on a Becton Dickinson FACSCalibur benchtop flow cytometer with a 488 nm excitation wavelength and the 530/30 (FL1) emission filter. Flow cytometry samples were prepared by placing approximately 0.5 µL of pelleted cells in 750 µL phosphate-buffered saline (PBS)—bovine serum albumin (BSA) (PBS at pH 7.4, with 1 mg/mL BSA). Statistical analysis to determine significant differences in expression levels was performed with the two-tailed unpaired Student's t test.

Quantitative PCR

RNA was isolated from yeast cells with the RNeasy Mini Total RNA Purification Kit (Qiagen, Valencia, Calif.) and on-column digestion with the RNase-Free DNase Set (Qiagen) was performed for 30 minutes to eliminate contaminating DNA. RNA concentrations were measured and 0.5 µg used to generate cDNA using the OmniScript RT Kit (Qiagen) with RNaseOUT recombinant ribonuclease inhibitor (Invitrogen, Carlsbad, Calif.), and oligo (dT)$_{20}$ primer (Invitrogen). RNA was stored at −80° C. and cDNA stored at −20° C. Quantitative PCR was performed with the QuantiTect SYBR Green PCR Kit (Qiagen) by adding 1 µL cDNA to each 50 µL reaction containing 25 µL QuantiTect SYBR Green PCR Master Mix, 20 µL RNase-free H$_2$O, 1.5 µL of each primer (at 10 µM), and 1 µL of a 10 nM fluorescein calibrant. Expression levels were normalized to the ACT1 housekeeping gene with the primers 5'-TTTGTCCTTGTACTCT-TCCG-3' (SEQ ID NO:2) and 5'-GTAAATTGGAAC-GACGTGAG-3' (SEQ ID NO:3). NHA1 (5'-GTTACGATGGAGAAGAGACAG-3' (SEQ ID NO:4) and 5'-CCAGGTTTCATTTCTTCCTC-3' (SEQ ID NO:5)), PMA1 (5'-TATTGTTACTGTCGTCCGTG-3' (SEQ ID NO:6) and 5'-GCTTACCGTTCATCAATCTG-3' (SEQ ID NO:7)), and RPP0 (5'-GTGTTCCCATCTTCTATCTT-3' (SEQ ID NO:8) and 5'-GTGACCGACAGATGGCAAGG-3' (SEQ ID NO:9)) genes were also analyzed. $\Delta\Delta C_t$ values were calculated by the equation $\Delta\Delta C_t = \Delta C_{t,ref} - \Delta C_{t,sample}$ where the reference is the WT cultures grown in 1× medium without refeeding and sampled at 24 hours post-induction. For a given sample, $\Delta C_t = C_{t,gene} - C_{t,ACT1}$ where $C_{t,gene}$ is the threshold cycle for amplification of a given gene and $C_{t,ACT1}$ is the threshold cycle for amplification of ACT1. Thus $\Delta\Delta C_t > 0$ corresponds to an upregulated gene in terms of PCR cycles, and quantitative data and statistics are reported in this form in Table 1. An estimated fold change of $2^{\Delta\Delta Ct}$ assuming 100% amplification efficiency for all genes is also given in Table 1 for approximate comparison but carries no quantitative value. PCR was performed on a Bio-Rad iCycler iQ Real-Time PCR Detection System and data analysis was facilitated with iCycler iQ Optical System Software (Bio-Rad, Hercules, Calif.). For comparison, cultures not expressing a heterologous protein were also collected and analyzed at 72 hours. Duplicate cultures were evaluated for each culture condition to generate the standard error reported. As with protein quantification, statistical significance was determined with the two-tailed unpaired Student's t test. The experimental trends were confirmed in two independent experiments.

Results

Overexpression of RPP0 Leads to Increased GFP Yields at 72 Hours

Figure 6:
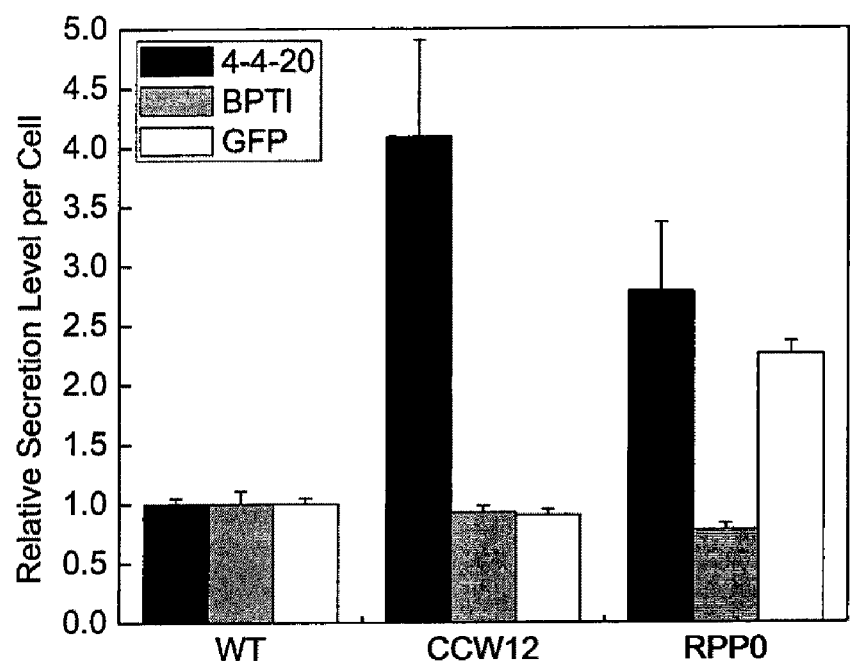
FIG. 6. Effects of CCW12 and RPP0 overexpression on secretion of heterologous proteins after 72 hours of protein induction. All secretion levels were normalized to cell density which does not significantly vary between different cultures. For each protein, secretion levels with an overexpressed gene are normalized to secretion levels of the corresponding wild-type (WT) strain that contains the pRS-316 plasmid in place of the pRS316-GAL1-cDNA construct where cDNA is either CCW12 or RPP0. Data is representative of triplicate cultures from at least two independent experiments.

Using low-copy CEN-based plasmids, secretion from *S. cerevisiae* yields approximately 1 mg/L 4-4-20 (Shusta, E. V., et al. Nat Biotechnol. 1998. 16(8)773-7), 3 mg/L GFP (Huang, D. and Shusta, E. V. Biotechnol Prog. 2005. 21(2) 349-57), and 5 mg/L BPTI (Parekh, R, et al. Protein Expr Purif. 1995. 6(4)537-45) without secretion-enhancing genetic modifications to the yeast strain. In order to evaluate the generality of the genes previously identified to increase protein secretion levels, all five genes (CCW12, CWP2, ERO1, RPP0, and SED1) were overexpressed and assessed for their effects on GFP and BPTI secretion and compared to the increases previously seen for 4-4-20 (Wentz, A. E. and Shusta, E. V. Appl Environ Microbiol. 2007. 73(4)1189-98). Of the five genes, only RPP0 overexpression led to reproducible increases (2.3-fold) in GFP secretion levels after 72 hours of protein induction when compared to a WT yeast strain also expressing GFP (FIG. 1). The other four genes had no impact on the GFP expression levels as represented by data for CCW12 overexpression, and none of the five genes had a positive impact on BPTI secretion (FIG. 1 and data not shown). These data contrasted with those observed for 4-4-20 where both CCW12 and RPP0 enhanced secretion levels (FIG. 6 and Wentz, A. E. and Shusta, E. V., Appl Environ Microbiol. 2007. 73(4)1189-98). With the RPP0-mediated increases observed for both GFP (2.3 fold) and 4-4-20 (2.9-fold), we next monitored expression levels over the entire three-day period to begin to understand the mechanism by which elevated expression of the RPP0 gene may impact expression levels of heterologous proteins.

Secretion Time Courses for 4-4-20 and GFP Differ

Rpp0p is a vital subunit for assembly of the ribosome stalk and lowered levels of P0 protein have been shown to lead to a reduction in the translational activity of ribosomes (Santos, C. and Ballesta, J. P. J Biol Chem. 1994. 269(22)15689-96; Krokowski, D., et al. Biochim Biophys Acta. 2005. 1724(1-2)59-70). An initial hypothesis was therefore that under conditions of heterologous protein expression, Rpp0p became a limiting component of the stalk assembly. Thus, under conditions of RPP0 overexpression we expected improved translational activity leading to elevated levels of protein synthesis and secretion throughout the entire induction period. To test this theory, we first assayed secretion levels at various time points after switching to galactose-containing induction medium (FIG. 7). Expression levels for 4-4-20 from WT yeast achieved a plateau beginning after 30 hours of induction while the RPP0 overexpressing cultures continued to secrete 4-4-20 throughout the entire time course (FIGS. 7A and 7B).

In contrast, maximum GFP secretion occurs near 40 hours of induction for both WT and RPP0 yeast cultures (FIGS. 7A and 7C). Unlike the 4-4-20 secretion dynamics, both WT and RPP0 overexpressing cultures achieve a similar maximum value within error. However, after achieving this maximum, levels of GFP in the supernatant substantially decline for the WT cultures at 72 hours ($p<0.05$), while RPP0 overexpressing, GFP-producing cultures lack a statistically significant loss ($p>0.6$) of GFP from the supernatant. No significant differences in cell growth were observed in either the 4-4-20 or GFP secreting systems (FIG. 7D). The differences in the secretion profiles for 4-4-20 and GFP suggested alternative roles for RPP0 in achieving the elevated yields observed for both proteins at 72 hours of induction. In addition, the mechanism by which overexpressing RPP0 provided higher secretion levels at 72 hours could involve increased protein production and/or decreased loss of protein.

Figure 8:
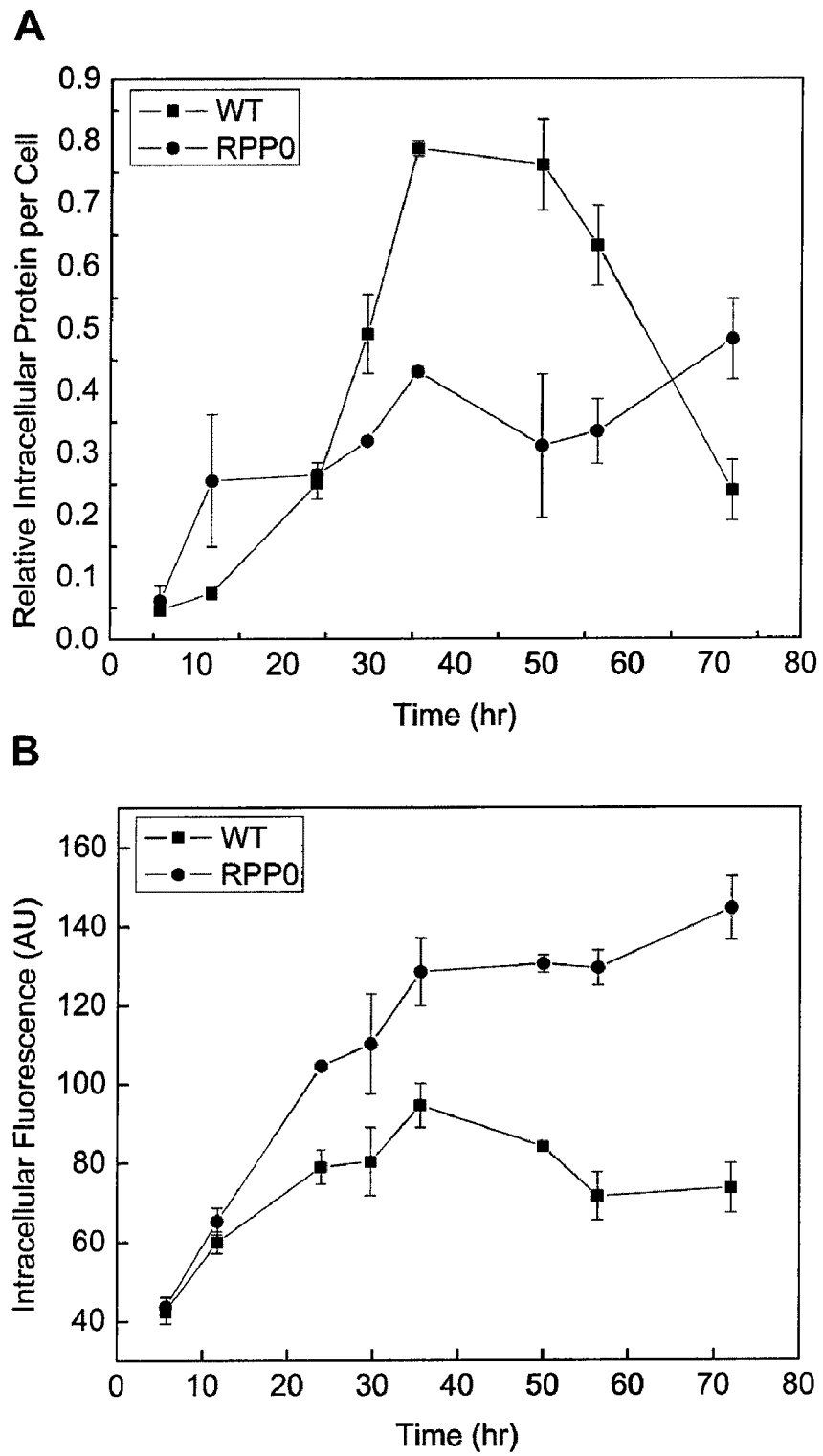
FIGS. 8A and B. Intracellular GFP levels for (A) full-length and (B) active protein. Full-length intracellular levels were measured by resolving cell lysate via SDS-PAGE and quantitative Western blotting with independent duplicate cultures. Active protein levels were quantified by measuring fluorescent levels of triplicate cultures of GFP-expressing cells with flow cytometry. All intracellular levels are representative of triplicate experiments. WT, wild-type; RPP0, cultures overexpressing RPP0.

Intracellular GFP Levels Suggest more Efficient Protein Folding with RPP0 Overexpression The secretion results observed for GFP indicated that RPP0 overexpression primarily limited protein loss, but did not appear to increase secretion. These data were counter to our hypothesis that RPP0 overexpression could facilitate protein synthesis and hence, secretion. To further examine the process, the total and active intracellular levels of GFP were analyzed in detail. Cultures overexpressing RPP0 actually had decreased levels of total GFP retained in the cells until late induction times (FIG. 8A) when protein loss begins to dominate secretion levels (FIG. 7C). Interestingly, the RPP0 overexpressing cultures retained equal or elevated levels of active GFP throughout the 72-hour induction time (FIG. 8B), suggesting RPP0 overexpression could yield a higher percentage of intracellular GFP that is properly folded, although higher secretion yields were not observed until late times for GFP.

To further investigate how RPP0 might yield a higher percentage of active intracellular protein and ultimately improved GFP yields, the impact of the unfolded protein response (UPR) was next evaluated. As the yeast secretory pathway becomes saturated and proteins accumulate within the ER, the UPR can be initiated via the Hac1p transcription factor, resulting in upregulation of 380 genes including chaperones and foldases that work to alleviate the stress (Travers, K. J., et al. Cell. 2000. 101(3)249-58). Upregulation of the UPR has also been shown to benefit secretion of heterologous proteins (Valkonen, M, et al. Appl Environ Microbiol. 2003. 69(4)2065-72). The effects of RPP0 overexpression on GFP production after 3-day induction were thus evaluated using a hac1Δ deletion strain. Upon RPP0 overexpression with a deficient UPR (RPP0-hac1Δ, data not shown), secretion levels were identical to those observed with an intact UPR (RPP0 in FIG. 6). However, levels of full-length and active protein retained intracellularly after three days were both increased (3- and 2.5-fold, respectively) in the RPP0-hac1Δ strain (data not shown). Non-RPP0 overexpressing strains experienced similar effects upon HAC1 deletion (data not shown). Thus, as with increases in intracellular active GFP in RPP0 overexpressing cultures in the intact UPR strain (FIG. 8B), a further increase in active protein accumulation inside the hac1Δ yeast cell did not yield increased secretion, and an improved UPR response through RPP0 overexpression does not appear to be responsible for the elevated intracellular levels of active GFP or the late stage improvement in GFP yields.

Intracellular levels of both the RPP0 transcript and its protein product were next analyzed to investigate any possible correlations to phenomena observed in heterologous protein levels during the induction time period. In order to explore increased Rpp0p and RPP0 gene transcript levels, total protein and RNA were isolated from cultures secreting GFP or 4-4-20 at 24 and 72 hours post-induction. Within the first 24 hours of protein induction, efficient secretion of protein is occurring for both WT and RPP0 overexpression strains, whereas at 72 hours post-induction, the cellular secretion machinery has significantly slowed or ceased operating, particularly in the WT case (FIGS. 7B and 7C). Thus, differences in gene expression at these two time points could help explain the different secretion profiles. Quantitative PCR was performed to confirm an increase in RPP0 transcript levels between WT and RPP0-overexpressing clones. Transcript levels for RPP0 were clearly increased in all RPP0-overexpressing cultures with 16-fold higher mRNA levels than WT cultures for both 4-4-20 and GFP samples at both 24 and 72 hours. Although RPP0 transcript levels were substantially elevated, probing for intracellular levels of the Rpp0p protein by Western blotting revealed no significant differences between WT and RPP0-overexpressing yeast throughout the entire time course as both WT and RPP0 yeast strains had similar upregulation of the Rpp0p protein during the first 48 hours of induction (data not shown). This finding is corroborated by a previous report in which GAL1-driven overexpression of RPP0 while yielding higher mRNA levels, resulted in negligible increases in Rpp0p protein levels (Santos, C. and Ballesta, J. P. J Biol Chem. 1994. 269(22)15689-96).

Correlation between Lowered pH and Loss of Secreted Protein

Figure 9:
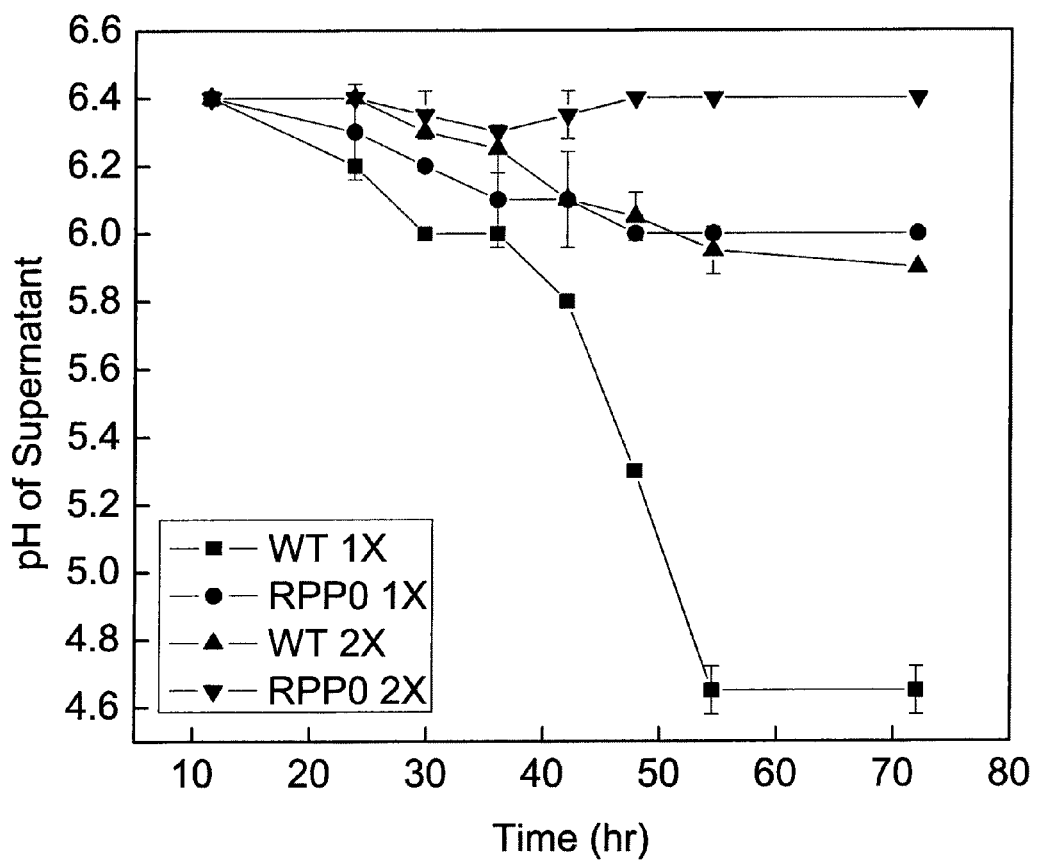
FIG. 9. Effects of buffering capacity and RPP0 overexpression on supernatant pH. WT, wild-type; RPP0, cultures overexpressing RPP0; 1×, cells induced in medium with 1× buffering capacity (50 mM phosphate); 2×, cells induced in 2× medium with double the buffering capacity (100 mM phosphate). Reported values are for 4-4-20 supernatants, but GFP supernatants had similar pH values. Data represents duplicate cultures from duplicate experiments.

With no apparent direct link between intracellular heterologous protein accumulation, at least for GFP, to argue for increased secretion upon RPP0 overexpression, we instead focused our efforts on a possible dominant protein loss term (FIGS. 7B and 7C). Previously, a loss of secreted protein has been shown to correlate with lowered pH that arose as a result of nitrogen starvation (Kobayashi, K., et al. J Biosci Bioeng. 2000. 89(1)55-61). Thus, the pH of both 4-4-20 and GFP supernatants were measured and results for both proteins were identical (FIG. 9). For much of the time course, the pH of WT supernatants (WT 1×) was substantially lower than that of RPP0 supernatants (RPP0 1×) with a significant decline beginning near 40 hours post-induction. Thus, the observed decrease in secreted protein levels correlated with a substantial decrease of pH, and RPP0 overexpression proved capable of minimizing this change in pH. To further strengthen the link between protein loss and lowered pH, the pH was better regulated by doubling the buffering capacity of the yeast medium. The secretion time-course experiments were repeated with media containing double the buffering capacity of the normal media (denoted by 2×). The WT yeast cells induced in 2× media experience a slight drop in pH (FIG. 9), and display similar pH behavior to RPP0 cultures grown in 1× medium. Moreover, RPP0 cultures grown in 2× medium (RPP0 2×) experience no change in pH, implicating an RPP0 function related to pH regulation.

Secretion profiles for WT yeast expressing 4-4-20 in 2× medium closely resemble the RPP0 cultures grown in 1× medium, while the RPP0 cultures in 2× medium achieve a slightly higher secretion level at 60 hours, but the same overall yield at 72 hours (FIG. 10A). Similarly, secretion levels for GFP in WT strains grown in 2× medium are comparable to those of RPP0 overexpressing strains in 1× medium, but depletion of secreted GFP in the supernatant between 60 and 72 hours was not at all evident with the 2× medium in WT strains (contrast FIGS. 7C and 10B). Moreover, RPP0 overexpression did not improve yields over the WT case under 2× conditions. Therefore, for 4-4-20 and GFP, preventing the acidification of the induction media either via RPP0 overexpression or increased buffering capacity of the media itself allowed full recovery of yield likely by limiting the loss of secreted product.

Exactly how RPP0 is able to prevent media acidification and coupled protein loss was unclear, and thus we investigated the expression levels of two proton pumps that could possibly be involved in the mechanism. The ability of cultures overexpressing RPP0 to better maintain extracellular pH (FIG. 9) potentially involves proton efflux from the cell. The yeast cell contains several proton pumps, including the $Na^+/H^+$ antiporter, Nha1p, and the plasma membrane $H^+$-ATPase, Pma1p. Quantitative PCR experiments performed with RNA samples collected from cells at 24 and 72 hours post-induction did not indicate a dramatic change in NHA1 expression over time or upon RPP0 overexpression (data not shown) suggesting a minor role for NHA1 in the RPP0 mechanism. In contrast, a dramatic increase in the transcription of PMA1 occurred between 24 and 72 hours in WT cells grown in 1× medium resulting in approximate 12- and 18-fold increases in mRNA for 4-4-20 and GFP expressing yeast, respectively (Table 3). At 72 hours post-induction, negative control cultures lacking expression of a heterologous protein showed similar levels of PMA1 mRNA as those for WT cells in 1× medium (data not shown) indicating the PMA1 response was independent of heterologous protein expression. In contrast, all other cultures with RPP0 overexpression and/or those grown in 2× media (Table 3 and data not shown), retain low levels of PMA1 transcription during the 3-day induction period. These results corroborate the pH profiles (FIG. 9) and their correlated secretion profiles (FIGS. 7 and 10) over the induction time course. Thus, RPP0 overexpression appears to prevent media acidification thereby reducing loss of secreted protein. However, these results do not eliminate the possibility that RPP0 overexpression may also be capable of increasing protein secretion at early induction times if the physiological conditions promoting acidification and protein loss were eliminated.

Replenishing Nutrients During Induction Promotes Higher Secretion

Although capable of limiting loss of secreted protein, increasing the buffering capacity of the induction medium in addition to RPP0 overexpression (RPP0 2×) proved ineffective at escalating the maximum secretion level of heterologous protein compared to RPP0 overexpression alone (RPP0 1×) (FIG. 10). These results suggested that RPP0 simply indirectly regulates the pH through PMA1, but may not directly assist in the secretion of heterologous proteins. However, starvation conditions can result in lowering of pH (Kobayashi, K., et al. J Biosci Bioeng. 2000. 89(1)55-61), and recent results obtained in our research group (Huang and Shusta, submitted) indicated that supplementing cultures with both yeast nitrogen base and amino acids can prevent the loss of secreted GFP during the final day of induction at several induction temperatures. Therefore, we tested whether such combined refeeding with pH regulation by induction in 2× medium or alternatively by RPP0 overexpression yielded different secretion profiles.

The addition of nutrients at 24 and 48 hours post-induction promoted cell growth with 30-50% increases in cell mass (FIG. 11A) and cells continued to secrete both 4-4-20 and GFP at late induction times upon refeeding (RF) (FIGS. 11B and 11C). Refeeding on its own also adequately prevented media acidification as all refed cultures maintained pH values above 6.0 (data not shown). In addition, refeeding prevents much of the PMA1 upregulation observed in WT1× strains (Table 3). On a per cell basis, the amount of 4-4-20 secreted from all refed RPP0 cultures (i.e., RPP0 1× RF and RPP0 2× RF) achieved higher maximum values compared to pH-regulated cultures (WT 2× RF) or to cultures not supplemented with additional nutrients (WT 1× and RPP0 1×), with a 3- to 4-fold increase in secretion level per cell when compared to the base case of WT 1× without refeeding (FIG. 11B). After taking the increased cell density into consideration, absolute 4-4-20 secretion levels increased by 6-fold (6 mg/L, RPP0 1× RF) compared to the WT 1× yield. In addition, since RPP0 1× RF behaves differently than WT 2× RF, it appears that RPP0 is providing more than just pH control under these conditions. Unlike the situation observed for 4-4-20, the maximum secreted values for GFP were similar among all refed cultures (FIG. 11C). However, none of the refed GFP cultures experienced a loss of secreted product in the final 12 hours of induction, and secretion levels were 3- to 4-fold higher at 72 hours post-induction when compared to WT 1× without refeeding (FIG. 11C). Taken together, the data reveal that overexpression of RPP0 combined with nutrient supplementation results in maximal secretion of both 4-4-20 and GFP, and that RPP0 appears to play contrasting roles in the secretion of these two proteins.

Discussion

Figure 11:
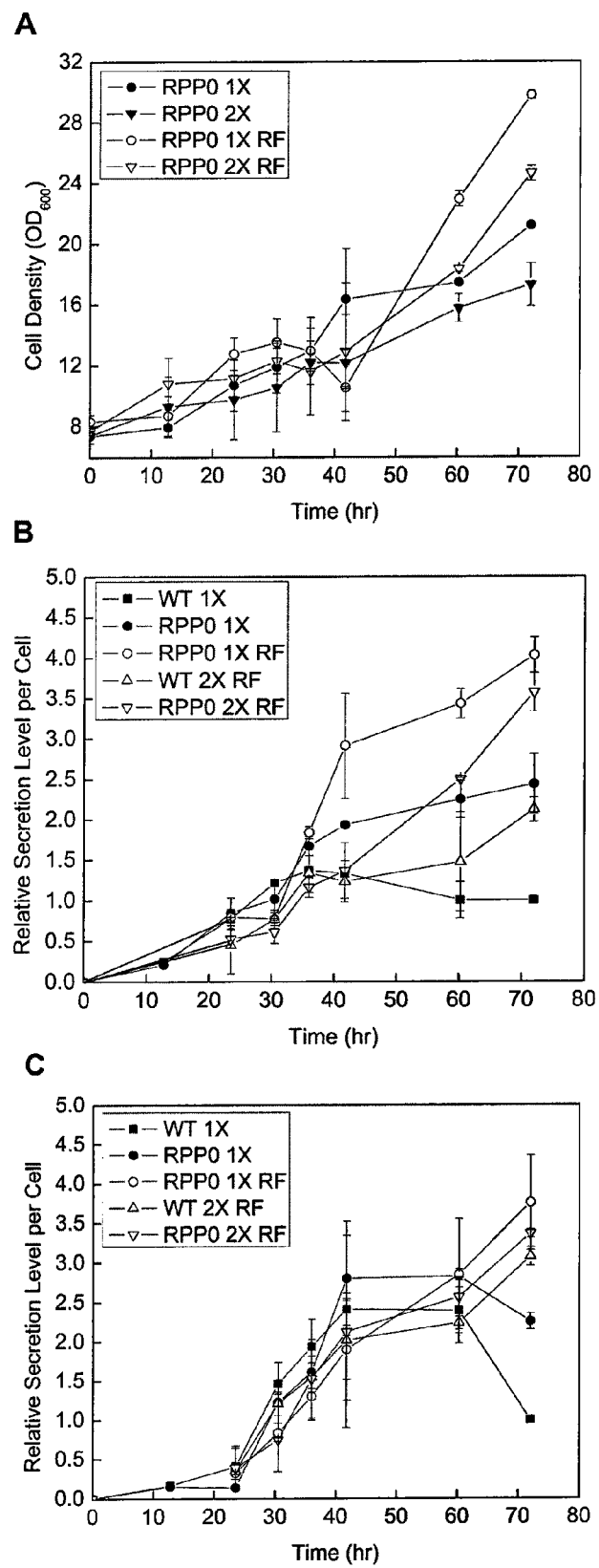
FIG. 11A-C. Secretion time-course for cultures supplemented with nutrients at 24 and 48 hours of induction. (A) Cell growth for 4-4-20 secreting cells is represented for both 1× and 2× media with RPP0 overexpression and with or without refeeding (RF). Cell growth profiles for wild-type (WT) cells closely resembled RPP0 overexpressing cultures for each media and/or refeeding condition and are thus not plotted. In addition, GFP-secreting cells behaved similarly in terms of cell growth. Protein secretion profiles for (B) 4-4-20 and (C) GFP include the 1× secretion data from FIG. 7 for comparison. All secretion levels were normalized to the WT 1× yield at 72 hours.

Evaluation of the generality of five secretion enhancers revealed that only RPP0 overexpression increased secretion levels for 4-4-20 and GFP, and no significant improvements were obtained for secretion of BPTI (FIG. 1). Overexpression of RPP0 significantly impacts secretion of 4-4-20 over much of the 72-hour induction time while providing a modest increase in GFP yields only at late induction times. Insights into the role of RPP0 overexpression on increasing heterologous protein secretion were explored in this work and revealed what appear to be differing mechanisms for the two analyzed proteins. For both 4-4-20 and GFP secreting yeast, RPP0 overexpressing clones achieve a higher maximum secretion level than WT at 72 hours (FIGS. 6 and 7) via a pH dependent mechanism, a phenomenon which is likely due in part to minimization of the protein loss. However, with 4-4-20 secretion, RPP0 overexpression appeared to also promote higher protein production in addition to preventing protein loss under conditions of refeeding (FIG. 11).

Although Rpp0p is an important ribosomal stalk subunit required for ribosome activity (Santos, C. and Ballesta, J. P. J Biol Chem. 1994. 269(22)15689-96), we did not observe any change in the total intracellular levels of protein indicating that translational effects were not resulting in the observed secretion increases. Since the amount of active intracellular protein was elevated in RPP0 overexpressing strains, we then explored UPR effects with the hypothesis that the expression of beneficial UPR components could somehow be facilitated by RPP0 overexpression. Experiments examining the effects of RPP0-overexpression in a hac1Δ strain showed no change in GFP secretion although intracellular full-length product and active GFP levels were approximately 3- and 2.5-fold higher, respectively, in the hac1Δ strain compared to the parent strain having an intact UPR. These results indicated the UPR plays a role in GFP processing possibly by regulating degradation (Travers, K. J., et al. Cell. 2000. 101(3)249-58; Oyadomari, S., et al. Cell. 2006. 126(4)727-39), but a link between the overexpression of RPP0 and upregulation of beneficial UPR processing components via the HAC1 gene does not appear to exist as increased intracellular levels of active protein were seen in the absence of a functioning UPR. Yet these results cannot rule out the ability of RPP0 overexpression itself to initiate an alternative cellular stress response that could impact protein folding and/or secretion levels. For example, it has been shown that multicopy overexpression of RPP0 enhanced Rpp0p levels 3-fold and resulted in a 2.5-fold increase in the expression of a protein regulated by a model heat shock element (HSE) promoter sequence (Kryndushkin, D. S., et al. J Biol Chem. 2002. 277(26)23702-8), and expression of Rpp0p in the absence of the P1/P2 ribosome stalk proteins results in Rpp0p aggregation, increased thermal tolerance and elevated mRNA levels of genes encoding heat shock response proteins HSP42 and HSP 26 (Krokowski, D., et al. Biochim Biophys Acta. 2005. 1724(1-2)59-70; Krokowski, D., et al. Mol Microbiol. 2006. 60(2)386-400).

Although increases in Rpp0p protein levels were not detected in our bulk cell lysate fractions, we cannot rule out differential localization and the potential of extraribosomal functions known to exist for many ribosomal proteins (Wool, I. G. Trends Biochem Sci. 1996. 21(5)164-5; Naora, H. Immunol Cell Biol. 1999. 77(3)197-205). Evidence of extraribosomal phenomena for Rpp0p homologs include DNA-repair activity mediated by the Drosophila P0 protein (Yacoub, A., et al. Nucleic Acids Res. 1996. 24(21)4298-303), as well as the interaction of yeast Rpp0p with a putative yeast integral membrane protein (Aruna, K., et al. J Biosci. 2004. 29(1)33-43). In addition, P0 proteins have been found at the surface of yeast and mammalian cells (Yoshio, T., et al. J Rheumatol. 1996. 23(7)1311-2; Singh, S., etal. Mol Biochem Parasitol. 2002. 119(1)121-4). These cell-surface interactions could possible serve to mediate the mechanism by which RPP0 overexpression is capable of impacting secretion of the proteins discussed in this study. Finally, given its propensity to aggregate in the absence of other ribosomal stalk proteins (Krokowski, D., et al. Biochim Biophys Acta. 2005. 1724(1-2)59-70; Krokowski, D.; Boguszewska, A., et al. Mol Microbiol. 2006. 60(2)386-400), excess Rpp0p may form aggregates that are rapidly cleared and hence undetectable in our sampling, but that are effective in triggering the stress responses detailed above.

Maintaining low intracellular levels of GFP that have a higher percent activity by lowering the induction temperature (20° C., same temperature as that used in this study) has recently been shown to correlate with increased secretion levels (Huang and Shusta, submitted). Thus the intracellular observations in FIGS. 8A and 8B and the increased amount of active protein in hac1Δ strains would suggest the potential for higher secretion yields with RPP0 overexpression. However, higher GFP yields are not observed until late induction times. One explanation for this observation is that an additional obstacle exists in the yeast secretory pathway that prevents properly folded GFP from exocytosis when produced at high levels. As observed previously (Huang, D. and Shusta, E. V. Appl Environ Microbiol. 2006. 72(12)7748-59), intracellular full-length GFP levels reported in FIG. 8A include both mature GFP as well as non-Golgi processed GFP (pro-GFP), but very little GFP that has not yet entered the ER. Earlier times (e.g., 24 hours post-induction) contain more pro-GFP while later times have approximately equal ratios of both pro-GFP and mature protein (data not shown). Therefore, overexpression of RPP0 may increase productive processing to active GFP, but a large fraction of the proteins, though fully mature and active, cannot efficiently traverse the entire secretory pathway and successfully secrete into the medium. The general phenomenon of protein accumulation has been observed previously as large amounts (10-15 mg/L) of GFP and GFP fusion proteins were found accumulated in an active form (Huang, D. and Shusta, E. V. Appl Environ Microbiol. 2006. 72(12)7748-59).

Both 4-4-20 (at 36 hours) and GFP (at 42 hours) stop accumulating in the culture medium. This could be a result of secretion cessation and/or increased loss. Previous results indicate that the secretory pathway is still capable of full function under conditions of 20° C. induction at long induction times, but a protein loss limits final titers (Huang and Shusta, submitted). Interestingly, this loss term can be alleviated either by RPP0 overexpression, increasing the buffering capacity of the protein induction media, or supplementing amino acids and a nitrogen source during induction. The dramatic pH decrease observed in WT cells induced in 1× media (FIG. 9) is consistent for both proteins, and overexpression of RPP0 inhibits acidification of the induction medium, a phenomenon that has previously been linked to post-secretion protein degradation (Kobayashi, K., et al. J Biosci Bioeng. 2000. 89(1)55-61). Modulating the media acidification with RPP0 overexpression or increased buffering capacity of the media sufficiently limited protein loss, and supplementing these systems with additional nutrients successfully promoted higher secretion yields indicating an operational secretion pathway. The data suggest that the primary culprit for media acidification is upregulation of the PMA1 gene (Table 3) which encodes a plasma membrane $H^+$-ATPase (Rao, R., et al. Ann N Y Acad Sci. 1992. (671) 195-203; Serrano, R. Mol Cell Biochem. 1978. 22(1)51-63) that has been shown to be activated during nitrogen starvation (Benito, B., et al. FEBS Lett. 1992. 300(3)271-4). Reducing Pma1p expression 3-fold has been shown to reduce the rate of amino acid uptake by approximately 4-fold (Cid, A., et al. Curr Genet. 1987. 12(2)105-10), implicating the role of Pma1p in generating a proton gradient that promotes uptake of nutrients during a starvation response. It should be noted that protein loss observed here is indeed cell-dependent and not simply a function of protein stability in the low pH culture medium (Huang and Shusta, submitted). Interestingly, while expression of heterologous proteins generally increases stress on the yeast cell (Kauffman, K. J., et al. Biotechnol Prog. 2002. 18(5)942-50; Cudna, R. E., et al. Biotechnol Bioeng. 2003. 81(1)56-65) responses to other stresses such as heat shock and oxidative stress can lead to PMA1 downregulation (Kim, I. S., et al. J Microbiol. 2006. 44(5)492-501; Piper, P. W., et al. Cell Stress Chaperones. 1997. 2(1)12-24). Thus, PMA1 upregulation and media acidification are likely not a direct result of heterologous protein expression, but instead correspond to a lack of available nutrients. This conclusion is further supported by the fact that yeast cells lacking heterologous protein expression also displayed significantly increased transcription of PMA1 and by the observation that refeeding alone prevents media acidification and PMA1 upregulation.

Finally, RPP0 though somehow clearly linked to pH homeostasis also appears to operate by multiple mechanisms for 4-4-20 compared with GFP. When starvation is taken out of the equation by refeeding, RPP0 provides little additional benefit to GFP secretion levels. In contrast, 4-4-20 secretion with both refeeding and RPP0 overexpression increases the per cell yield substantially indicating that RPP0 can function in increasing protein secretion in addition to decreasing pH-dependent protein loss. Although the exact mechanism for this substantial improvement was not fully elucidated here, RPP0 overexpression suffices to alleviate loss of secreted proteins, and combined with nutrient supplementation, increased yields of heterologous proteins can be achieved.

TABLE 3

| | | PMA1 transcript levels* | | | |
|---|---|---|---|---|---|
| Protein | Time | WT 1X | RPP0 1X | WT 2X | WT 1X RF |
| 4-4-20 | 24 hr | 0.0 ± 0.3 (1.0) | NC | NC | NC |
| | 72 hr | 3.6 ± 0.2 (12) | −1.5 ± 0.2 (−2.8) | NC | NC |
| GFP | 24 hr | 0.0 ± 0.1 (1.0) | −0.5 ± 0.1 (−1.4) | −0.8 ± 0.1 (−1.7) | NC |
| | 72 hr | 4.2 ± 1.8 (18) | −1.7 ± 0.2 (−3.2) | NC | 1.1 ± 0.4 (2.1) |

*Expression of the PMA1 gene under each condition is normalized to the 24-hour wild-type (WT) for 4-4-20 or GFP, respectively. Quantitative $\Delta\Delta C_t$ values (see Materials and Methods) are tabulated as Mean ± SD for samples that differ (p < 0.1) from WT 1X at 24 hours for a given protein (4-4-20 or GFP) and estimates for fold differences are in parentheses. Samples not having a statistically significant change compared to WT 1X at 24 hours are indicated by NC (no change). For both $\Delta\Delta C_t$ values and fold changes, positive numbers correspond to PMA1 upregulation while negative numbers indicate PMA1 downregulation when compared to the 24-hour WT situation. RPP0, cells overexpressing RPP0; 1X, cells induced in 1X medium; 2X, cells induced in 2X medium; RF, cells were refed during the induction time-course at 24 and 48 hours.

TABLE 4

Nucleotide Sequences from www.yeastgenome.org

CCW12 (SEQ ID NO: 10):
ATGCAATTTTCTACTGTCGCTTCTATCGCCGCTGTCGCCGCTGTCGCTTCTGCCGCTGCT
AACGTTACCACTGCTACTGTCAGCCAAGAATCTACCACTTTGGTCACCATCACTTCTTGT
GAAGACCACGTCTGTTCTGAAACTGTCTCCCCAGCTTTGGTTTCCACCGCTACCGTCACC
GTCGATGACGTTATCACTCAATACACCACCTGGTGCCCATTGACCACTGAAGCCCCAAAG
AACGGTACTTCTACTGCTGCTCCAGTTACCTCTACTGAAGCTCCAAAGAACACCACCTCT
GCTGCTCCAACTCACTCTGTCACCTCTTACACTGGTGCTGCTGCTAAGGCTTTGCCAGCT
GCTGGTGCTTTGTTGGCTGGTGCCGCTGCTTTGTTGTTGTAA

RPP0 (SEQ ID NO: 11):
ATGGGAGGCATTCGTGAAAAGAAAGCTGAATACTTTGCTAAATTAAGAGAATACTTGGAA
GAATACAAGTCTTTGTTCGTTGTTGGTGTTGACAATGTTTCTTCCCAACAAATGCACGAA
GTCAGAAAGGAATTGAGAGGCAGAGCTGTCGTCTTGATGGGTAAGAACACCATGGTTAGA
AGAGCCATCAGAGGTTTCTTATCCGACTTGCCAGACTTCGAAAAGTTGTTGCCTTTTGTC
AAAGGTAACGTTGGTTTCGTTTTCACTAACGAACCATTGACTGAAATCAAGAACGTTATT
GTCTCTAACAGAGTTGCTGCTCCAGCCAGAGCTGGTGCCGTTGCTCCAGAAGACATCTGG
GTTAGAGCCGTCAACACTGGTATGGAACCAGGTAAGACTTCTTCTTCCAAGCTTTGGGT
GTCCCAACCAAGATTGCCAGAGGTACCATTGAAATTGTTTCTGATGTCAAGGTCGTTGAC
GCCGGTAACAAGGTCGGTCAATCTGAAGCTTCCTTGTTGAACTTGTTGAACATCTCTCCA
TTCACTTTCGGTTTGACTGTTGTTCAAGTTTACGACAACGGTCAAGTGTTCCCATCTTCT
ATCTTGGATATCACCGATGAAGAATTGGTTTCTCACTTCGTTTCCGCTGTCAGCACCATT
GCTTCTATCTCTTTGGCTATTGGTTACCCAACCTTGCCATCTGTCGGTCACACTTTGATC
AACAACTACAAGGACTTGTTAGCTGTTGCCATTGCTGCTTCCTACCACTACCCTGAAATT
GAAGATTTGGTTGACAGAATTGAAAACCCAGAAAAGTACGCTGCTGCTGCTCCAGCTGCT
ACCTCCGCTGCTTCCGGTGACGCTGCTCCAGCTGAAGAAGCTGCTGCTGAAGAAGAAGAA
GAATCTGATGACGACATGGGTTTCGGTTTATTCGATTAA

ERO1 (SEQ ID NO: 12):
ATGAGATTAAGAACCGCCATTGCCACACTGTGCCTCACGGCTTTTACATCTGCAACTTCA
AACAATAGCTACATCGCCACCGACCAAACACAAAATGCCTTTAATGACACTCACTTTTGT
AAGGTCGACAGGAATGATCACGTTAGTCCCAGTTGTAACGTAACATTCAATGAATTAAAT
GCCATAAATGAAAACATTAGAGATGATCTTTCGGCGTTATTAAAATCTGATTTCTTCAAA
TACTTTCGGCTGGATTTATACAAGCAATGTTCATTTTGGGACGCCAACGATGGTCTGTGC
TTAAACCGCGCTTGCTCTGTTGATGTCGTAGAGGACTGGGATACACTGCCTGAGTACTGG
CAGCCTGAGATCTTGGGTAGTTTCAATAATGATACAATGAAGGAAGCGGATGATAGCGAT
GACGAATGTAAGTTCTTAGATCAACTATGTCAAACCAGTAAAAAACCTGTAGATATCGAA
GACACCATCAACTACTGTGATGTAAATGACTTTAACGGTAAAAACGCCGTTCTGATTGAT
TTAACAGCAAATCCGGAACGATTTACAGGTTATGGTGGTAAGCAAGCTGGTCAAATTTGG
TCTACTATCTACCAAGACAACTGTTTTACAATTGCCGAAACTGGTAATCATTGGCAAA
GATGCATTTTATAGACTTGTATCCGGTTTCCATGCCTCTATCGGTACTCACTTATCAAAG
GAATATTTGAACACGAAAACTGGTAAATGGGAGCCCAATCTGGATTTGTTTATGGCAAGA
ATCGGGAACTTTCCTGATAGAGTGACAAACATGTATTTCAATTATGCGTTGTAGCTAAG
GCTCTCTGGAAAATTCAACCATATTTACCAGAATTTTCATTCTGTGATCTAGTCAATAAA
GAAATCAAAACAAATGGATAACGTTATTTCCCAGCTGGACACAAAAATTTTTAACGAA
GACTTAGTTTTTGCCAACGACCTAAGTTTGACTTTGAAGGACGAATTCAGATCTCGCTTC
AAGAATGTCACGAAGATTATGGATTGTGTGCAATGTGATAGATGTAGATTGTGGGCAAA
ATTCAAACTACCGGTTACGCAACTGCCTTGAAAATTTTGTTTGAAATCAACGACGCTGAT
GAATTCACCAAACAACATATTGTTGGTAAGTTAACCAAATATGAGTTGATTGCACTATTA
CAGACTTTCGGTAGATTATCTGAATCTATTGAATCTGTTAACATGTTCGAAAAAATGTAC
GGGAAAAGGTTAAACGGTTCTGAAAACAGGTTAAGCTCATTCTTCCAAAATAACTTCTTC
AACATTTTGAAGGAGGCAGGCAAATCGATTCGTTACACCATAGAGAACATCAATTCCACT
AAAGAAGGAAAGAAAAAGACTAACAATTCTCAATCACATGTATTTGATGATTTAAAAATG
CCCAAAGCAGAAATAGTTCCAAGGCCCTCTAACGGTACAGTAAATAAATGGAAGAAAGCT
TGGAATACTGAAGTTAACAACGTTTTAGAAGCATTCAGATTTATTTATAGAAGCTATTTG
GATTTACCCAGGAACATCTGGGAATTATCTTTGATGAAGGTATACAAATTTTGGAATAAA
TTCATCGGTGTTGCTGATTACGTTAGTGAGGAGACACGAGAGCCTATTTCCTATAAGCTA
GATATACAATAA

TABLE 4-continued

Nucleotide Sequences from www.yeastgenome.org

CWP2 (SEQ ID NO: 13):
ATGCAATTCTCTACTGTCGCTTCCGTTGCTTTCGTCGCTTTGGCTAACTTTGTTGCCGCT
GAATCCGCTGCCGCCATTTCTCAAATCACTGACGGTCAAATCCAAGCTACTACCACTGCT
ACCACCGAAGCTACCACCACTGCTGCCCCATCTTCCACCGTTGAAACTGTTTCTCCATCC
AGCACCGAAACTATCTCTCAACAAACTGAAAATGGTGCTGCTAAGGCCGCTGTCGGTATG
GGTGCCGGTGCTCTAGCTGCTGCTGCTATGTTGTTATAA

SED1 (SEQ ID NO: 14):
ATGAAATTATCAACTGTCCTATTATCTGCCGGTTTAGCCTCGACTACTTTGGCCCAATTT
TCCAACAGTACATCTGCTTCTTCCACCGATGTCACTTCCTCCTCTTCCATCTCCACTTCC
TCTGGCTCAGTAACTATCACATCTTCTGAAGCTCCAGAATCCGACAACGGTACCAGCACA
GCTGCACCAACTGAAACCTCAACAGAGGCTCCAACCACTGCTATCCCAACTAACGGTACC
TCTACTGAAGCTCCAACCACTGCTATCCCAACTAACGGTACCTCTACTGAAGCTCCAACT
GATACTACTACTGAAGCTCCAACCACCGCTCTTCCAACTAACGGTACTTCTACTGAAGCT
CCAACTGATACTACTACTGAAGCTCCAACCACCGGTCTTCCAACCAACGGTACCACTTCA
GCTTTCCCACCAACTACATCTTTGCCACCAAGCAACACTACCACCACTCCTCCTTACAAC
CCATCTACTGACTACACCACTGACTACACTGTAGTCACTGAATATACTACTTACTGTCCA
GAACCAACCACTTTCACCACAAACGGTAAGACTTACACCGTCACTGAACCAACCACATTG
ACTATCACTGACTGTCCATGCACCATTGAAAAGCCAACAACCACATCAACCACCGAATAC
ACTGTAGTCACTGAGTACACTACTTACTGTCCAGAACCAACCACTTTCACCACAAACGGT
AAGACTTACACCGTCACTGAACCAACCACTTTGACTATCACTGACTGTCCATGTACTATT
GAAAAGAGCGAAGCCCCTGAGTCTTCTGTCCCAGTTACCGAATCTAAGGGCACTACCACC
AAAGAAACAGGTGTTACTACCAAACAAACCACAGCCAACCCAAGTCTAACCGTCTCCACA
GTCGTCCCAGTTTCATCCTCTGCTTCTTCTCATTCCGTTGTCATCAACAGTAACGGTGCT
AACGTCGTCGTTCCAGGTGCTTTAGGTTTGGCTGGTGTTGCTATGTTATTCTTATAA

Example III

Data with Single-cDNA Overexpression for Various Classes of Proteins

We questioned whether the method of the present invention was appropriate for classes of protein other than those disclosed in Wentz and Shusta, 2007.

Figure 12:
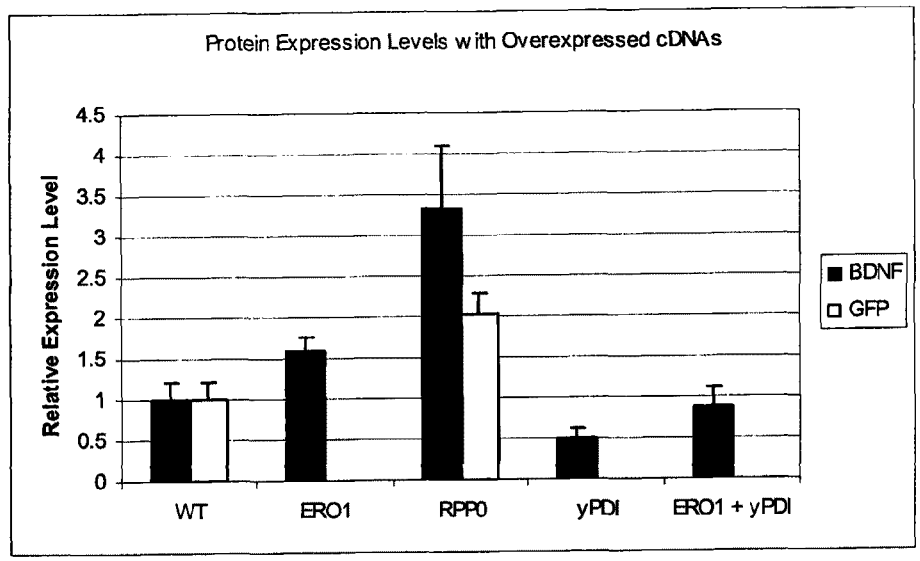
FIG. 12. Bar graph of protein expression levels (BDNF and GFP) with overexpressed cDNAs.

FIG. 12 is a tabulation of our results. Referring to FIG. 12, relative secreted expression levels of BDNF (brain-derived neurotrophic factor) and GFP (green fluorescent protein) with various yeast genes overexpressed are disclosed. All values are normalized to the corresponding WT secretion level where the cells are transformed with pRS316 instead of pRS316-cDNA. yPDI is yeast protein disulfide isomerase, an ER-localized protein that helps proteins achieve their proper fold by rearranging disulfide bonds in the protein construct.

CCW12 led to no increases in BDNF expression, and CWP2 and SED1 were not tested with this protein. Note that yPDI actually hurts BDNF expression, but in cooperation with ERO1, expression levels are slightly recovered. (ERO1, on its own, can improve BDNF secretion.) In the yeast cell, Ero1p supplies the oxidizing equivalents to yPDI.

GFP expression with RPP0 has been reproduced over multiple experiments, and the expression levels vary from 2- to 4-fold improvements over WT. None of the other four cDNAs resulted in reproducibly higher GFP secretion when overexpressed, but this is not surprising given GFP has a relatively high basal secretion level in yeast.

Expression of the bovine pancreatic trypsin inhibitor (BPTI) protein was also tested, but none of the overexpressed cDNA were capable of enhancing its secretion levels. Again, this protein has high basal secretion levels. This implies that the secretion enhancers work best with the proteins that have low expression yields, oftentimes as a result of low stability or folding efficiency.

Example IV

Data for Heterologous Protein Expression with Two cDNAs Overexpressed

Figure 13:
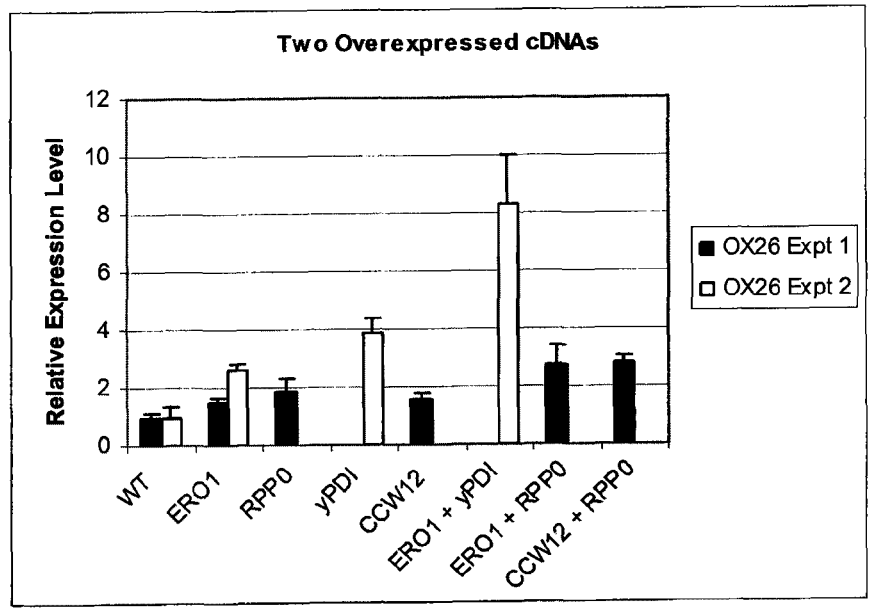
FIG. 13. Bar graph of heterologous protein expression using two over-expressed cDNAs.

We questioned whether combinations of the genes or homologs would prove more effective than use of an individual gene or homolog. To that end, we examined the relative secretion levels of OX26 scFv with two cDNA genes overexpressed. FIG. 13 tabulates the results of this experiment. All expression levels are normalized to the expression level of OX26 without cDNA overexpression.

BDNF expression levels are improved when yPDI and ERO1 are co-overexpressed in the yeast cell (FIG. 12) compared with yPDI alone as described above, but not compared with the single ERO1 overexpression case. In contrast, with the OX26 scFv, ERO1 and yPDI act together synergistically. With OX26, additive effects are also observed with overexpression of two cDNAs (ERO1+RPP0 or CCW12+RPP0) when compared to single cDNA overexpression systems.

Combining CCW12 and ERO1 resulted in no further increases in OX26 expression compared to CCW12 or ERO1 alone. Additionally, the 4-4-20 scFv was tested in one experiment with the CCW12 and RPP0 combination, but no improvements were seen with two cDNAs overexpressed when compared to the single-cDNA overexpression systems.

Example V

Prophetic Design of Yeast Strain with Three cDNAs Overexpressed

One may wish to design a yeast strain with three cDNAs overexpressed and expect to see a successful increase in protein product. Creation of the yeast strain with three overexpressed cDNAs may utilize the URA3 Blaster technique and the pδ-UB (Lee, F. W. and Da Silva, N. A. *Biotechnol Prog* 1997, 13, (4), 368-73) plasmid acquired from Nancy Da Silva (UC Irvine). The construct works by cutting the plasmid at the δ-integration sequence and transforming yeast cells where the linearized plasmid will integrate at one of the repetitive chromosomal DNA δ sequences. The pδUB plasmid was first modified to include both the AvrII and AflII restriction enzyme sites in the XhoI cut site within the δ-integration sequence. We inserted new enzyme sites into the δ-integration sequence because the sites present in the original pδ-UB plasmid were also present in our cDNAs (CCW12, RPP0, ERO1).

Next, one would insert display enhancing cDNAs (including the GAL1 promoter) into the modified pδ-UB structure at either the KpnI or the SacI sites. These plasmids would be linearized and transformed into yeast (BJ5464) one at a time. As discussed in Lee and Da Silva (N. A. *Biotechnol Prog* 1997, 13, (4), 368-73), clones successfully integrating the construct can be selected for based on the URA3 nutritional marker contained in the plasmid. Once clones are identified as integrating the construct, cells are grown on 5-FOA (5-fluoro orotic acid) containing media where the URA3 gene is removed via homologous recombination as it is flanked by two identical hisG repeats. However, the rest of the integrated construct (including our GAL1-cDNA) remains. Therefore, the strain will be built one cDNA at a time, but will ultimately contain all three cDNAs under the GAL1 promoter. Secretion levels of the heterologous proteins will then be tested as described in Wentz and Shusta (2007, Supra).

We also have a strain that has yPDI constitutively overexpressed (YVH10). One might alter this strain with the three integrated, overexpressed cDNAs. Both YVH10 and BJ5464 yeast strains are documented in Wentz and Shusta 2007, Supra. Yeast PDI has been previously demonstrated by us and others to assist in protein secretion. Hence, we expect synergistic effects from the four gene overexpression strain (in YVH10) compared with the three gene overexpression system (in BJ5464).

As there are multiple possibilities for bottlenecks through the secretory pathway, we expect overexpression of multiple genes that increase protein secretion to be beneficial. The three cDNAs we focus on in future work (CCW12, ERO1, and RPP0) are likely functioning in different areas of the cell (cell wall rearrangement, protein folding in the ER, protein translation). Although the new strain may not increase secretion levels of all of our proteins, we do not expect their expression levels to deteriorate. For the low-expression proteins, we expect to see higher secretion levels with the new strain. These expectations are based on raw data collected and presented above when we co-overexpressed two cDNAs.

We claim:

1. A method of enhancing secretion of heterologous protein of interest in a yeast cell comprising the steps of:

a. engineering a first yeast cell to overexpress at least two genes selected from the group consisting of *S. cerevisiae* CCW12, CWP2, SED1, RPPO and ER01, *K. lactis* XP_455980.1 (CCW12), *C. albicans* CCW12, *P. stipitis* CCW12, *K. lactis* ER01, *P. stipitis* ERO1, *S. pombe* ERO12 and ERO11, *Mus musculus* ERO1LB, *Homo sapien* ERO1LB, *K. lactis* XP_451800.1 (RPPO), *P. stipitis* RPPO, *C. albicans* XP_888730.1 (RPPO), *S. pombe* RPPO, *Mus musculus* ARBP, and *Homo sapien* RPLPO, wherein the two genes encode two functionally different proteins, and wherein said heterologous protein of interest differs in structure and function from the proteins engineered to overexpress in said first yeast cell; and b. supplying the yeast cell with a nucleic acid encoding said heterologous protein of interest, wherein the secretion of said heterologous protein of interest is increased by the overexpression of said at least two genes in the first yeast cell in step a relative to the secretion of said heterologous protein in a second yeast cell that does not overexpress said at least two genes selected from the group consisting of *S. cerevisiae* CCW12, CWP2, SED1, RPPO and ER01, *K. lactis* XP_455980.1 (CCW12), *C. albicans* CCW12, *P. stipitis* CCW12, *K. lactis* ER01, *P. stipitis* ERO1, *S. pombe* ERO12 and ERO11, *Mus musculus* ERO1LB, *Homo sapien* ERO1LB, *K. lactis* XP_451800.1 (RPPO), *P. stipitis* RPPO, *C. albicans* XP_888730.1 (RPPO), *S. pombe* RPPO, *Mus musculus* ARBP, and *Homo sapien* RPLPO.

2. The method of claim 1 wherein at least three genes are chosen.

3. The method of claim 2 wherein at least three genes are CCW12, ERO1, and RPPO.

4. The method of claim 1 wherein the yeast is selected form the group consisting of *S. cerevisiae, P. pastoris*, and *K. lactis*.

5. The method of claim 1 wherein the gene is selected from the group consisting of CCW12, CWP2, SED1, RPPO, and ERO1 and the yeast is *S. cerevisiae*.

6. The method of claim 1 wherein the heterologous protein has expression levels of 3 mg/L or more in the yeast cell in the absence of enhanced secretion.

7. The method of claim 1 wherein the heterologous protein contains disulfide bonds.

8. The method of claim 1 wherein the heterologous protein has an expression level of 1 mg/L or less in the absence of enhanced secretion.

9. The method of claim 1 wherein the heterologous protein is a member of the immunoglobulin superfamily including antibodies, T-cell receptors, MHC, cell surface receptors involved in the immune response, adhesion receptors and cytokines.

10. The method of claim 1 wherein protein expression is induced via an inducible promoter.

11. The method of claim 10 wherein the increase is at least 2 fold.

12. The method of claim 1 wherein protein expression is increased at least 1.5 fold.

13. The method of claim 12 wherein the increase is at least 4 fold.

14. The cell of claim 13 wherein the gene is selected from the group consisting of CCW12, CWP2, SED1, RPPO, and ERO1 and the yeast is *S. cerevisiae*.

15. The cell of claim 14 wherein the cell is engineered to overexpress CCW12, ERO1 and RPPO.

16. The cell of claim 13 wherein the yeast is selected from the group consisting of *S. cerevisiae, P. pastoris*, and *K. lactis*.

17. An engineered yeast cell expressing a heterologous protein of interest wherein said yeast cell is engineered to overexpress at least two genes selected from the group consisting of CCW12, CWP2, SED1, RPPO, ERO1 and *K. lactis* XP_455980.1 (CCW12), *C. albicans* CCW12, *P. stipitis* CCW12, *K. lactis* ERO1, *P. stipitis* ERO1, *S. pombe* ERO12 and ERO11, *Mus musculus* ERO1LB, *Homo sapien* ERO1LB, *K. lactis* XP_451800.1 (RPPO), *P. stipitis* RPPO, *C. albicans* XP_888730.1 (RPPO), *S. pombe* RPPO, *Mus musculus* ARBP, and *Homo sapien* RPLPO, wherein said two genes encode two functionally different proteins, wherein said heterologous protein of interest differs in structure and function from the proteins produced by said overexpressing genes, and wherein said heterologous protein is expressed from a gene sequence that has been transformed into the yeast cell, and wherein the secretion of said heterologous protein is enhanced compared to a non-engineered yeast cell.

* * * * *

UNITED STATES PATENT AND TRADEMARK OFFICE
CERTIFICATE OF CORRECTION

| | | |
|---|---|---|
| PATENT NO. | : 8,034,607 B2 | Page 1 of 1 |
| APPLICATION NO. | : 12/209656 | |
| DATED | : October 11, 2011 | |
| INVENTOR(S) | : Eric V. Shusta and Alane E. Wentz | |

It is certified that error appears in the above-identified patent and that said Letters Patent is hereby corrected as shown below:

Column 11, line 33 "blofting" should be --blotting--

Signed and Sealed this
Third Day of April, 2012

David J. Kappos
*Director of the United States Patent and Trademark Office*